United States Patent
Yokoyama et al.

(10) Patent No.: US 8,642,189 B2
(45) Date of Patent: Feb. 4, 2014

(54) SUBSTITUTED BIPYRIDYL COMPOUND AND ORGANIC ELECTROLUMINESCENT DEVICE

(75) Inventors: Norimasa Yokoyama, Tsukuba (JP); Shuichi Hayashi, Tsukuba (JP); Makoto Nagaoka, Tsukuba (JP); Yoshio Taniguchi, Ueda (JP); Musubu Ichikawa, Ueda (JP)

(73) Assignees: Hodogaya Chemical Co., Ltd., Tokyo (JP); Shinshu University, National University Corporation, Matsumoto (JP)

( * ) Notice: Subject to any disclaimer, the term of this patent is extended or adjusted under 35 U.S.C. 154(b) by 177 days.

(21) Appl. No.: 12/735,885

(22) PCT Filed: Feb. 25, 2009

(86) PCT No.: PCT/JP2009/053396
§ 371 (c)(1),
(2), (4) Date: Aug. 24, 2010

(87) PCT Pub. No.: WO2009/107651
PCT Pub. Date: Sep. 3, 2009

(65) Prior Publication Data
US 2011/0001129 A1 Jan. 6, 2011

(30) Foreign Application Priority Data
Feb. 26, 2008 (JP) .................................. 2008-043788

(51) Int. Cl.
*H01L 51/54* (2006.01)

(52) U.S. Cl.
USPC ........... 428/690; 313/504; 313/505; 313/506; 546/18; 546/79; 546/81; 546/101; 548/418; 548/440; 428/917

(58) Field of Classification Search
USPC .................. 428/690, 917; 313/504, 505, 506; 546/18, 79, 81, 101; 548/418, 440
See application file for complete search history.

(56) References Cited

U.S. PATENT DOCUMENTS 7,964,293 B2 * 6/2011 Ono et al. .................... 428/690
(Continued)

FOREIGN PATENT DOCUMENTS

| JP | 2004-022334 A | 1/2004 | |
| JP | 2004-200162 | * 7/2004 | ............. H05B 33/14 |

(Continued)

OTHER PUBLICATIONS

Ichikawa, M. et. al., "Bipyridyl substituted triazoles as hole-blocking and electron-transporting materials for organic light-emitting devices," Organic Electronics 9 (2008) pp. 77-84.
Schilt, A. A., "New chromogens of the ferroin-type-I. Substituted triazines related to 6-cyano-2,2'-bipyridine," TALANTA, vol. 15, 1968, pp. 475 to 478.

(Continued)

*Primary Examiner* — Gregory Clark
(74) *Attorney, Agent, or Firm* — Edwards Wildman Palmer LLP; James E. Armstrong, IV; Nicholas J. DiCeglie, Jr.

(57) ABSTRACT

The invention provides an organic compound which shows an excellent electron-injecting/transporting performance, has a hole-blocking ability and shows a high stability as a film, that is, having excellent characteristics as a material for organic electroluminescent device having high efficiency and high durability; and provides an organic EL device comprising the compound and having high efficiency and high durability. The organic compound being a substituted bipyridyl compound represented by the general formula (1);

[Formula 1]

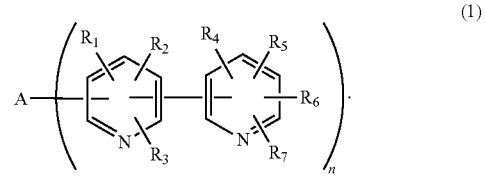

11 Claims, 4 Drawing Sheets

(56) References Cited

U.S. PATENT DOCUMENTS

| | | | |
|---|---|---|---|
| 2003/0137239 A1* | 7/2003 | Matsuura et al. ............. 313/503 |
| 2009/0102361 A1 | 4/2009 | Miki et al. |
| 2009/0134780 A1 | 5/2009 | Ono et al. |
| 2010/0090588 A1 | 4/2010 | Yokoyama et al. |

FOREIGN PATENT DOCUMENTS

| | | | | |
|---|---|---|---|---|
| JP | 2005-317297 | * | 11/2005 | ............. H05B 33/14 |
| JP | 2005-317297 A | | 11/2005 | |
| JP | 2008-120696 | * | 5/2006 | ........... C07D 213/22 |
| JP | 2008-120696 A | | 5/2008 | |
| WO | WO-2007/029696 A1 | | 3/2007 | |
| WO | WO-2007026847 A1 | | 3/2007 | |
| WO | WO 2007086552 | * | 8/2007 | ............. H01L 51/50 |
| WO | WO-2008023628 A1 | | 2/2008 | |
| WO | WO-2009/054253 A1 | | 4/2009 | |

OTHER PUBLICATIONS

Case, F. H., "The Preparation of Triazines Related to 6-Cyano-2,2'-bipyridine," The Journal of Organic Chemistry, vol. 31, 1966, pp. 2398-2400.

Medlycott, E. A. et al., "Minimal structural reorganization in the electrochemical oxidationof a dinuclear, double helical Cu(I) complex of a triazine-based pentadentate ligand," Chemical Communication, 2007, pp. 4884-4886.

International Search Report dated Apr. 7, 2009, issued for PCT/JP2009/053396.

Laure-Emmanuelle Perret-Aebi et al., "Efficient Synthesis of Chiral 2,2'-Bis-bipyridines," SYNLETT, vol. 5, May 3, 2002, pp. 773-774.

Laure-Emmanuelle Perret-Aebi et al., "Stereoselective Synthesis of a Topologically Chiral Molecule: The Trefoil Knot," Angewandte Chemie International Edition, vol. 43, No. 34, Aug. 27, 2004, pp. 4482-4485.

Supplementary European Search Report dated Feb. 23, 2012, issued for the corresponding European patent application No. 09715178.1.

* cited by examiner

SUBSTITUTED BIPYRIDYL COMPOUND AND ORGANIC ELECTROLUMINESCENT DEVICE

TECHNICAL FIELD

The present invention relates to a compound suitable for organic electroluminescent (EL) device, a self-emitting device favorable for various display devices, and to the device, and precisely to a substituted bipyridyl compound and to an organic EL device comprising the compound.

BACKGROUND ART

An organic EL device is a self-emitting device and has been actively studied, since it is light and excellent in the visibility and enables vivid display as compared with liquid-crystal devices.

In 1987, Eastman Kodak's C. W. Tang, et al. developed laminate structure devices in which the constitutive materials share various roles and have thereby put organic EL materials comprising organic materials into practical use. They laminated a fluorescent material capable of transporting electrons and an organic material capable of transporting holes, and thereby injected both charges into a fluorescent material layer for light emission, and obtained a high luminance of at least 1000 $cd/m^2$ at a voltage of 10 V or less (for example, see Patent Reference 1 and Patent Reference 2).
Patent Reference 1: JP-A 8-48656
Patent Reference 2: Japanese Patent No. 3194657

Up to the present, various improvements have been made for practical use of organic EL devices, and an electroluminescent device has come to attain high efficiency and durability, in which various roles are further subdivided to comprise an anode, a hole injection layer, a hole transport layer, a light-emitting layer, an electron transport layer, an electron injection layer and a cathode, as provided in that order on a substrate (for example, see Non-Patent Reference 1).
Non-Patent Reference 1: Preprint in 9th Seminar of the Japan Society of Applied Physics, pp. 55-61 (2001)

For the purpose of further improvement in luminous efficiency, use of a triplet exciton has been tried, and use of a phosphorescent material is being investigated (for example, see Non-Patent Reference 2).
Non-Patent Reference 2: Preprint in 9th Seminar of the Japan Society of Applied Physics, pp. 23-31 (0.2001)

A light-emitting layer may be formed by doping a charge-transporting compound generally referred to as a host material with a fluorescent material or a phosphorescent material. As described in the above-mentioned seminar preprints, the selection of organic materials in organic EL devices has a significant influence on various characteristics such as the efficiency and the durability of the devices.

In an organic EL device, the charges injected from both electrodes are recombined in the light-emitting layer to emit light. In this, however, since the hole mobility is higher than the electron mobility, there occurs a problem of efficiency reduction owing to passing of a part of holes through the light-emitting layer. Accordingly, an electron-transporting material in which the electron mobility is high is desired.

A typical light-emitting material, tris(8-hydroxyquinoline) aluminium (hereinafter abbreviated as $Alq_3$) generally serves also as an electron-transporting material, but it could not be said that the material may have a hole-blocking ability.

As a measure of preventing the passing of a part of holes through a light-emitting layer and increasing the probability of charge recombination in a light-emitting layer, there is known a method of inserting a hole-blocking layer. As a hole-blocking material, heretofore proposed are triazole derivatives (for example, see Patent Reference 3), bathocuproin (hereinafter abbreviated as BCP), mixed-ligand complexes of aluminium (BAlq) (for example, see Non-Patent Reference 2), etc.

For example, as an electron-transporting material having an excellent hole-blocking ability, proposed is 3-(4-biphenylyl)-4-phenyl-5-(4-t-butylphenyl)-1,2,4-triazole (hereinafter abbreviated as TAZ) (for example, see Patent Reference 3).
Patent Reference 3: Japanese Patent No. 2734341

TAZ has a large work function of 6.6 eV and has a high hole-blocking ability, and is therefore used as an electron-transporting hole-blocking layer to be laminated on the cathode side of the fluorescent light-emitting layer or the phosphorescence-emitting layer formed through vacuum evaporation, coating or the like, and contributes toward increasing the efficiency of organic EL devices (for example, see Non-Patent Reference 3).
Non-Patent Reference 3: Preprint in 28p-A-6 Lecture of the 50th Applied Physics-Associated Joint Lecture Presentation, p. 1413 (2003)

However, TAZ has a serious problem in that its electron transportability is low, and it must be combined with an electron-transporting material having a higher electron transportability in using it for constructing organic EL devices (for example, see Non-Patent Reference 4).
Non-Patent Reference 4: Journal of the Organic Molecule/Bioelectronics Section Committee of the Japan Society of Applied Physics, Vol. 11, No. 1, pp. 13-19 (2000)

BCP has a large work function of 6.7 eV and has a high hole-blocking ability, but has a low glass transition point (Tg) of 83° C., and therefore its film stability is poor, and accordingly, it could not be said that BCP may fully function as a hole-blocking layer. Accordingly, for a phosphorescent device, use of BAlq as the hole-blocking layer is proposed as a measure for life prolongation. The life of the device could be prolonged; however, since the work function of BAlq is 5.8 eV and is small, holes could not be efficiently trapped in the light-emitting layer, and the device could not be said to be sufficient owing to efficiency reduction therein as compared with a device comprising BCP.
Non-Patent Reference 5: 9th Lecture in the Organic Molecule/Bioelectronics Section Committee of the Japan Society of Applied Physics, pp. 23-31 (2001)

All the materials are insufficient in the stability of films thereof or insufficient in the function thereof of blocking holes. For improving the characteristics of organic EL devices, desired are organic compounds showing an excellent electron-injecting/transporting performance, an excellent hole-blocking ability and showing a high stability as thin films.

DISCLOSURE OF THE INVENTION

Problems that the Invention is to Solve

An object of the invention is to provide an organic compound which shows an excellent electron-injecting/transporting performance, has a hole-blocking ability and shows a high stability as a thin film, that is, having excellent characteristics as a material for organic electroluminescent device having high efficiency and high durability; and to provide an organic EL device comprising the compound and having high efficiency and high durability. The physical characteristics of the organic compound suitable to the invention are that the compound has (1) a good electron injection characteristic, (2) a high electron mobility, (3) an excellent hole-blocking ability, and is (4) stable as a thin film and (5) excellent in heat resistance. The physical characteristics of the device suitable to the invention are that the device has (1) a high luminous efficiency, (2) a low turn on voltage, and (3) a low practical drive voltage.

Means for Solving the Problems

For attaining the above-mentioned object, the present inventors have noted that, on the nitrogen atom thereof, an electrophilic pyridine ring has the ability to coordinate with a metal and is excellent in heat resistance, and have planned and chemically synthesized a substituted bipyridyl compound; and using the compound, the inventors have produced various organic electroluminescent devices experimentally, and have assiduously investigated and evaluated the characteristics of the devices and, as a result, have completed the present invention.

Specifically, the invention is a substituted bipyridyl compound represented by a general formula (1), and is an organic electroluminescent device having a pair of electrodes and having at least one organic layer sandwiched between them, wherein the compound is used as the constitutive material of at least one organic layer.

[Formula 1]

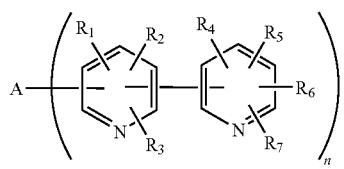
(1)

(wherein $R^1$ to $R^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a di- to tetra-valent, substituted or unsubstituted aromatic hydrocarbon group, a di- to tetra-valent, substituted or unsubstituted aromatic heterocyclic group, a di- to tetra-valent, substituted or unsubstituted condensed polycyclic aromatic group, or a trivalent group represented by the following general formula (2):

[Formula 2]

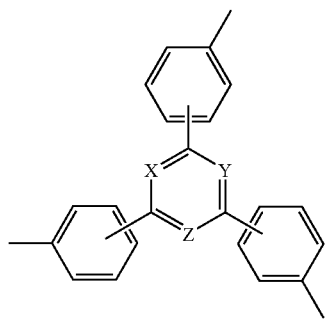
(2)

(wherein X, Y and Z each represents a carbon atom or a nitrogen atom); provided that when n=2, the two bipyridyl structures may direct bond to each other, and in the case, A is absent).

The aromatic hydrocarbon group, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group for A in the general formula (1) concretely include the following groups: a phenyl group, a biphenylyl group, a terphenylyl group, a tetrakisphenyl group, a styryl group, a naphthyl group, an anthryl group, an acenaphthenyl group, a fluorenyl group, a phenanthryl group, a pyrenyl group, a pyridyl group, a pyrimidyl group, a triazine group, a furanyl group, a pyronyl group, a thienyl group, a quinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolyl group.

The substituent for the substituted or unsubstituted aromatic hydrocarbon group, the substituted or unsubstituted aromatic heterocyclic group or the substituted or unsubstituted condensed polycyclic aromatic group for A in the general formula (1) concretely includes a fluorine atom, a chlorine atom, a cyano group, a hydroxyl group, a nitro group, and a linear or branched alkyl group having from 1 to 6 carbon atoms, and these may be further substituted.

The aromatic hydrocarbon group of the substituted or unsubstituted aromatic hydrocarbon group, the substituted or unsubstituted aromatic heterocyclic group or the substituted or unsubstituted condensed polycyclic aromatic group for R1 to R7 in the general formula (1) concretely include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a bipyridyl group, a pyrimidinyl group, a furanyl group, a pyronyl group, a thienyl group, a quinolyl group, an isoquinolyl group, a benzofuranyl group, a benzothienyl group, an indolyl group, a carbazolyl group, a benzoxazolyl group, benzothiazolyl group, a quinoxalyl group, a benzimidazolyl group, a pyrazolyl group, a dibenzofuranyl group, a dibenzothienyl group, a naphthyridinyl group, a phenanthrolinyl group, and an acridinyl group.

The substituent for the substituted or unsubstituted aromatic hydrocarbon group, the substituted or unsubstituted aromatic heterocyclic group or the substituted or unsubstituted condensed polycyclic aromatic group for R1 to R7 in the general formula (1) concretely includes a fluorine atom, a chlorine atom, a trifluoromethyl group, a linear or branched alkyl group having from 1 to 6 carbon atoms, a phenyl group, a biphenylyl group, a terphenyl group, a tetrakisphenyl group, a styryl group, a naphthyl group, a fluorenyl group, a phenanthryl group, an indenyl group, a pyrenyl group, a pyridyl group, a bipyridyl group, a pyrimidyl group, a quinolyl group, an isoquinolyl group, an indolyl group, a carbazolyl group, a quinoxalyl group, and a pyrazolyl group, which may be further substituted.

The substituted bipyridyl compound represented by the general formula (1) of the invention secures a higher transfer electron rate than conventional electron-transferring materials, and has an excellent hole-blocking ability and is stable as a thin film.

The substituted bipyridyl compound represented by the general formula (1) of the invention can be used as a constitutive material for the electron transport layer of an organic electroluminescent device (hereinafter abbreviated as organic EL device). Using the material having a higher electron injection/mobility than conventional materials brings about the advantages that the electron transportation efficiency from the electron transport layer to the light-emitting layer is improved, that the light luminous efficiency is improved, and that the drive voltage is lowered and the durability of organic EL devices is enhanced.

The substituted bipyridyl compound represented by the general formula (1) of the invention can be used as the constitutive material of the hole-blocking layer of an organic EL device. Using the material having an excellent hole-blocking ability, more excellent in electron transportability than conventional materials and highly stable as a thin film brings about the advantages that the drive voltage is lowered while high light luminous efficiency is secured, and that the current resistance is improved and therefore the maximum emission luminance of organic EL devices is thereby increased.

The substituted bipyridyl compound represented by the general formula (1) of the invention can be used as the constitutive material of the light-emitting layer of an organic EL device. Using the material of the invention that has more excellent electron transportability than conventional materials and has a broad band gap as the host material in the light-emitting layer and making the host material carry a fluorescent material or a phosphorescent material called a dopant therewith for the light-emitting layer brings about the advantage of realizing an organic EL device that has a lowered drive voltage and has improved light luminous efficiency.

The organic EL device of the invention comprises the substituted bipyridyl compound capable of securing more rapid electron transfer than conventional electron-transporting materials, having an excellent hole-blocking ability and stable as a thin film, and therefore realizes high efficiency and high durability.

Advantage of the Invention

The substituted bipyridyl compound of the invention secures rapid electron transfer, has an excellent hole-blocking ability and is stable as a thin film, and is therefore useful as a constitutive material for the electron transport layer, the hole-blocking layer or the light-emitting layer of an organic EL device. The organic EL device produced using the substituted bipyridyl compound secures the advantages that the light luminous efficiency is improved, that the drive voltage is lowered and the durability is improved.

DESCRIPTION OF REFERENCE NUMERALS

Figure 1:
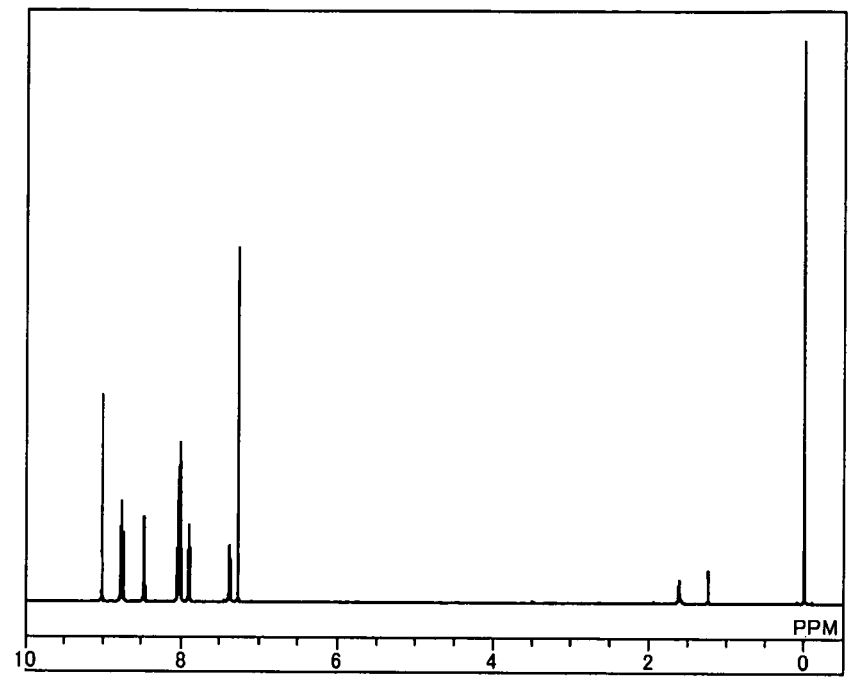
FIG. 1 This is a 1H-NMR chart of the compound (compound 6) of Example 1 of the invention.

1 Glass Substrate
2 Transparent Anode
3 Hole Transport Layer
4 Light-Emitting Layer
5 Hole-Blocking Layer
6 Electron Transport Layer
7 Electron Injection Layer
8 Cathode

BEST MODE FOR CARRYING OUT THE INVENTION

The substituted bipyridyl compounds of the invention are novel compounds, and these substituted bipyridyl compounds may be produced by reacting a boronic acid or a boronate that is produced through reaction of a halide of various aromatic hydrocarbon compounds, condensed polycyclic aromatic compounds or aromatic heterocyclic compounds with pinacol or bis(pinacolato)diboron (for example, see Non-Patent Reference 6), with various halogenopyridines in a mode of cross-coupling such as Suzuki coupling (for example, see Non-Patent Reference 7). Through triazine ring forming reaction of using sodium hydride for various aromatic hydrocarbon compounds, condensed polycyclic aromatic compounds or aromatic heterocyclic compounds having a nitrile group (for example, see Patent Reference 4), bipyridyl compounds with a triazine ring binding thereto may be produced.

Non-Patent Reference 6: J. Org. Chem., 60 7508 (1995)

Non-Patent Reference 7: Synth. Commun., 11, 513 (1981)

Patent Reference 4: JP-A 2004-284971

Specific examples of preferred compounds of the substituted bipyridyl compounds represented by the general formula (1) are shown below; however, the invention is not limited to these compounds.

[Formula 3]

(Compound 2)

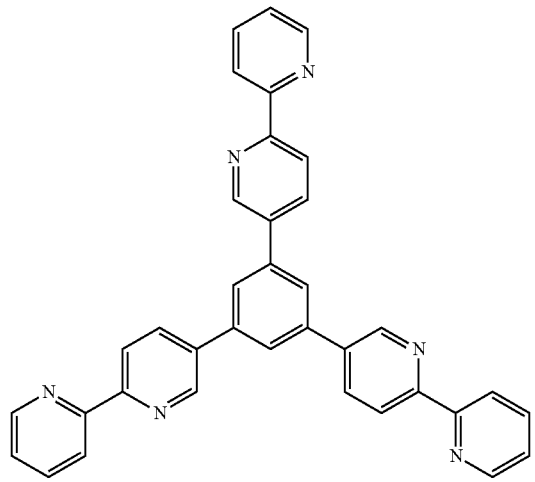

[Formula 4]
(Compound 3)
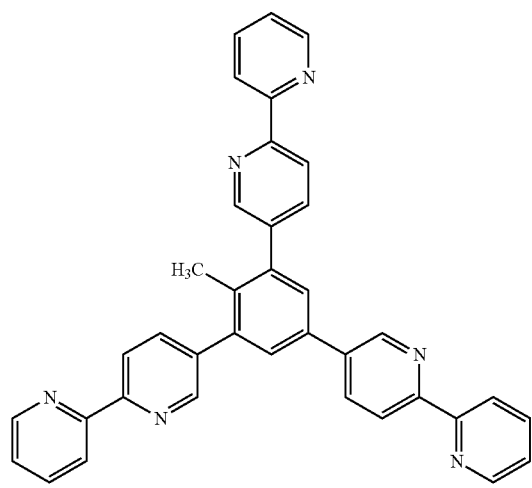
[Formula 5]
(Compound 4)
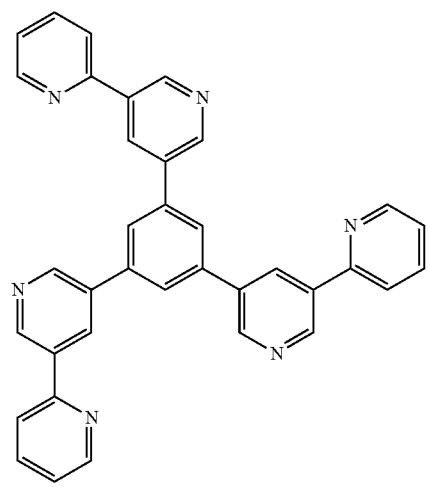
[Formula 6]
(Compound 5)
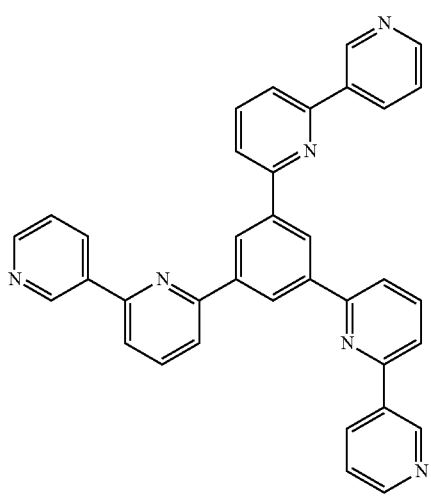
[Formula 7]
(Compound 6)
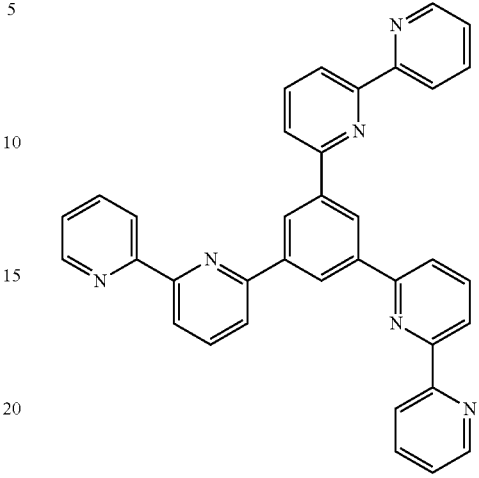
[Formula 8]
(Compound 7)
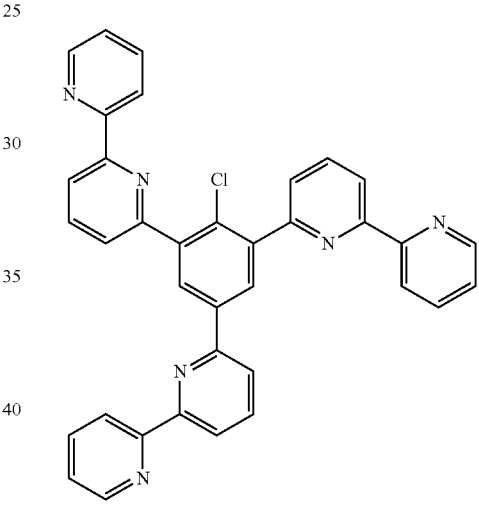
[Formula 9]
(Compound 8)
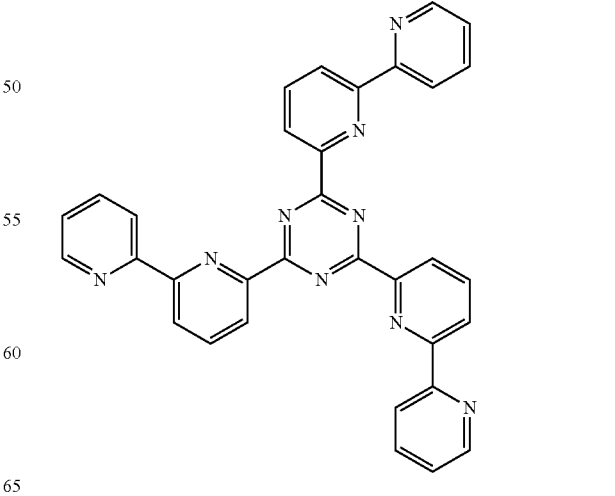

[Formula 10]
(Compound 9)
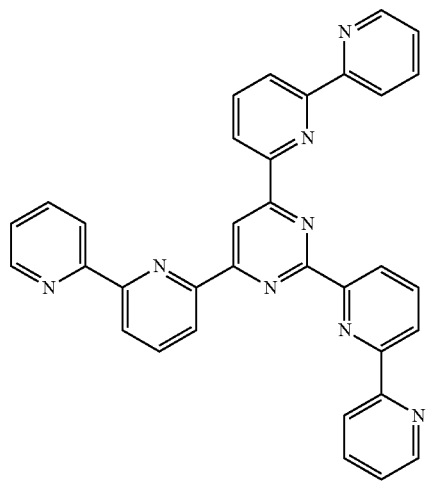
[Formula 11]
(Compound 10)
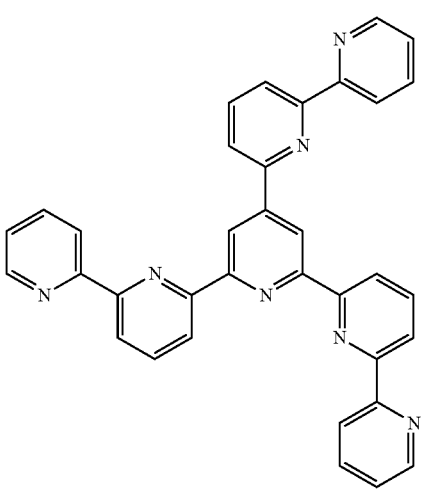
[Formula 12]
(Compound 11)
[Formula 13]
(Compound 12)
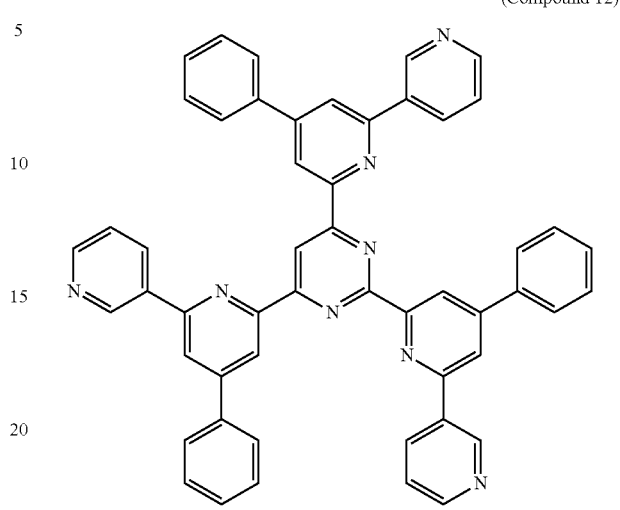
[Formula 14]
(Compound 13)
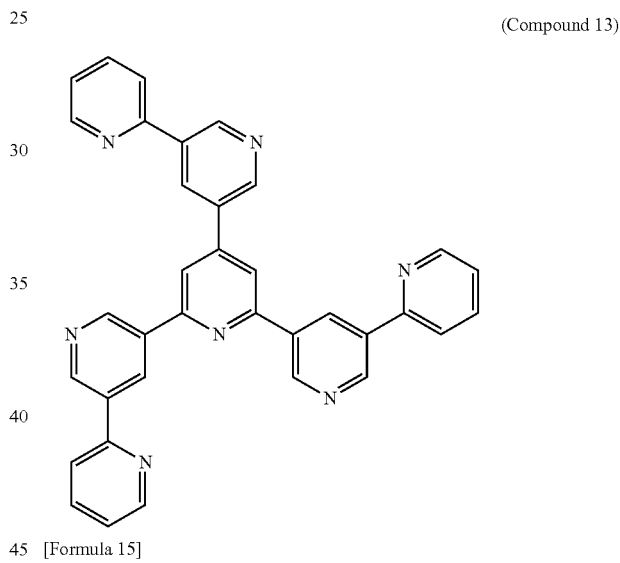
[Formula 15]
(Compound 14)
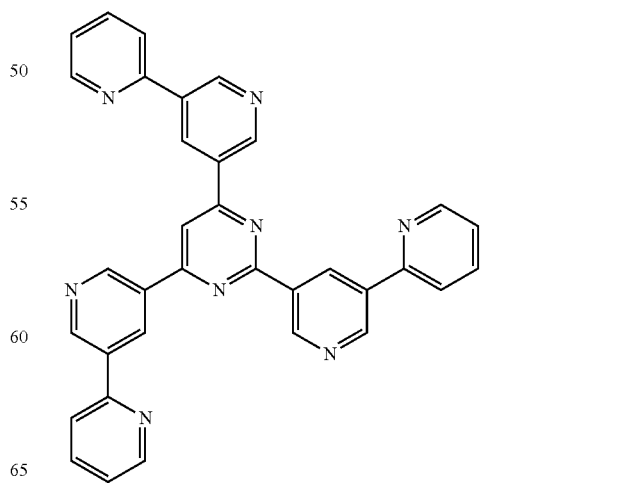

[Formula 16]
(Compound 15)
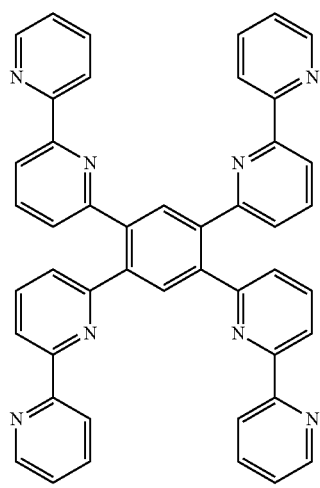
[Formula 17]
(Compound 16)
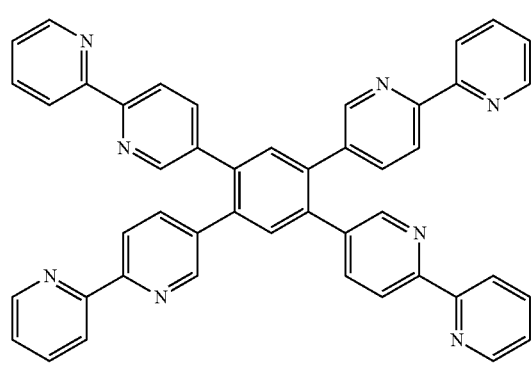
[Formula 18]
(Compound 17)
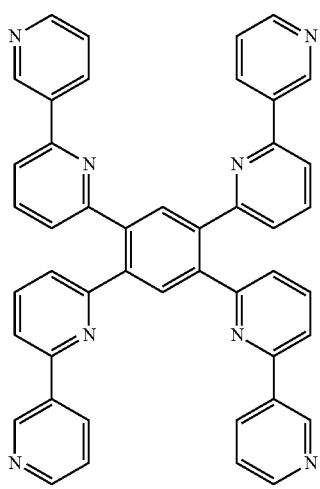
[Formula 19]
(Compound 18)
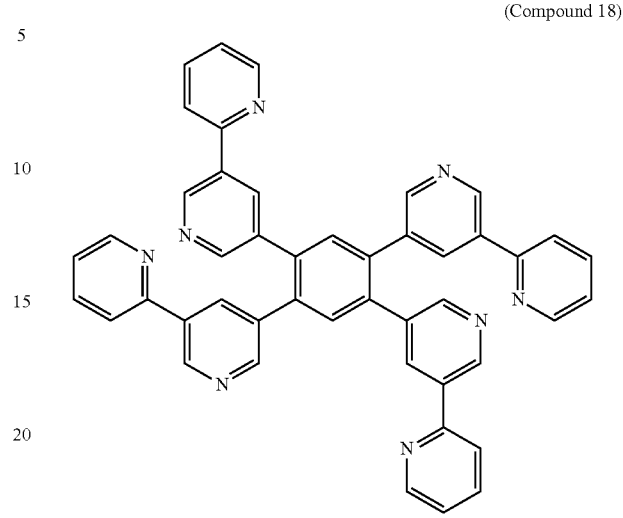
[Formula 20]
(Compound 19)
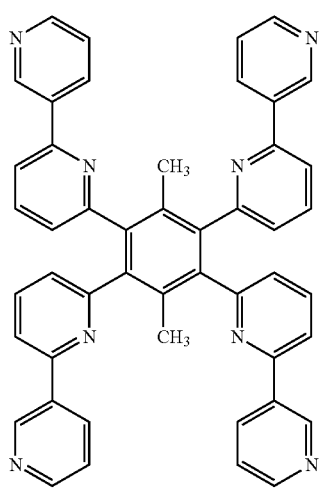
[Formula 21]
(Compound 20)
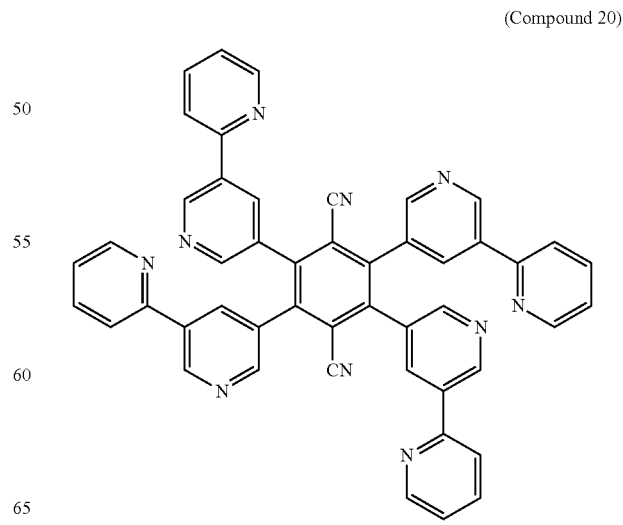

[Formula 22]
(Compound 21)
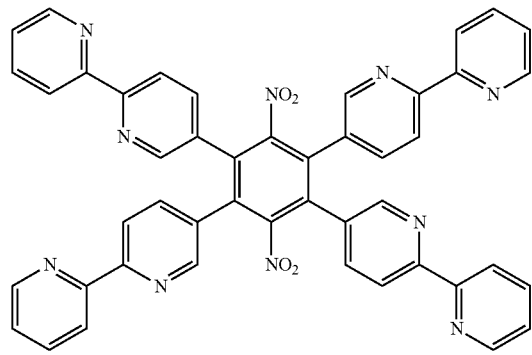
[Formula 23]
(Compound 22)
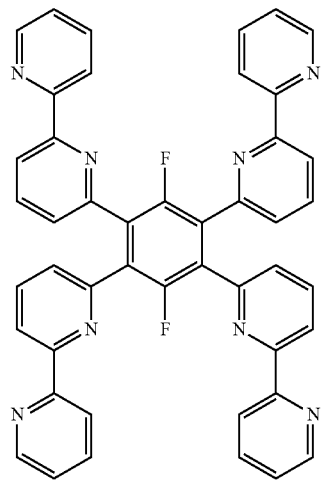
[Formula 24]
(Compound 23)
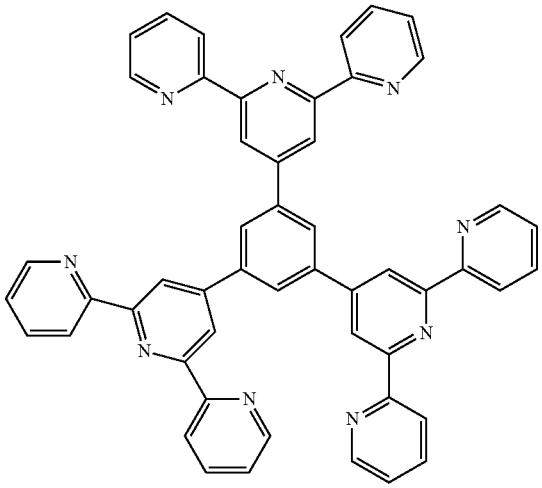
[Formula 25]
(Compound 24)
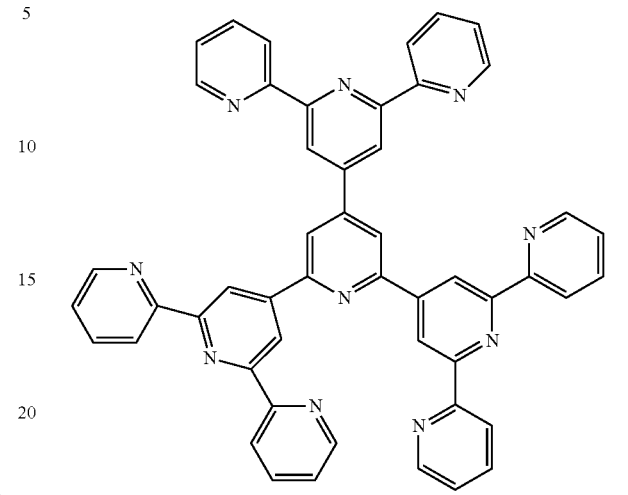
[Formula 26]
(Compound 25)
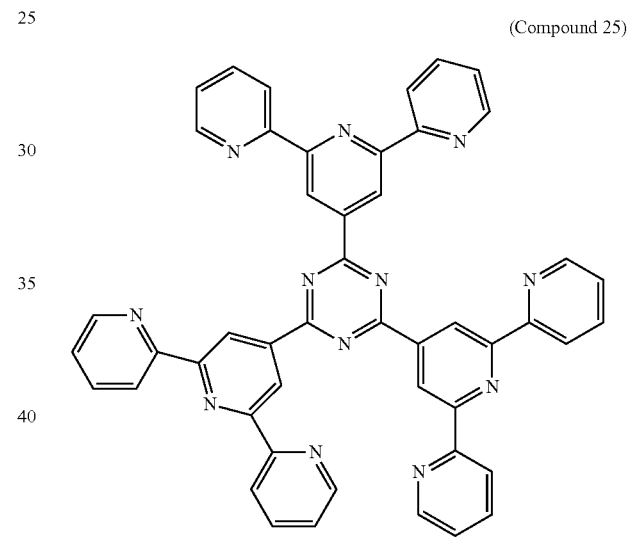
[Formula 27]
(Compound 26)
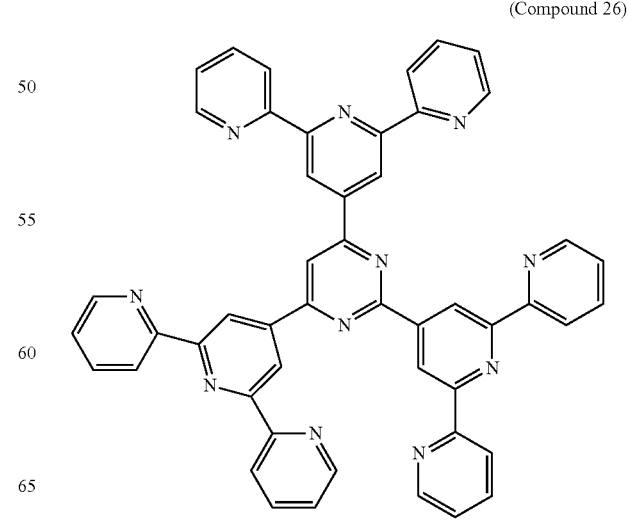

[Formula 28]
(Compound 27)
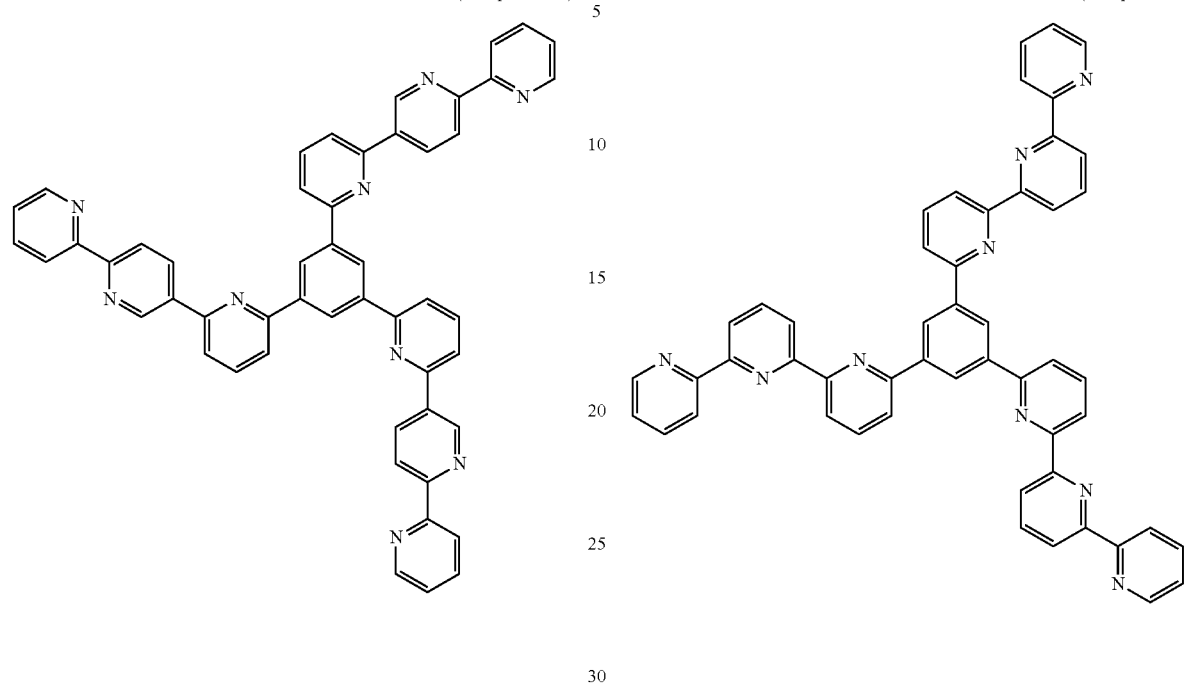
[Formula 29]
(Compound 28)
[Formula 30]
(Compound 29)
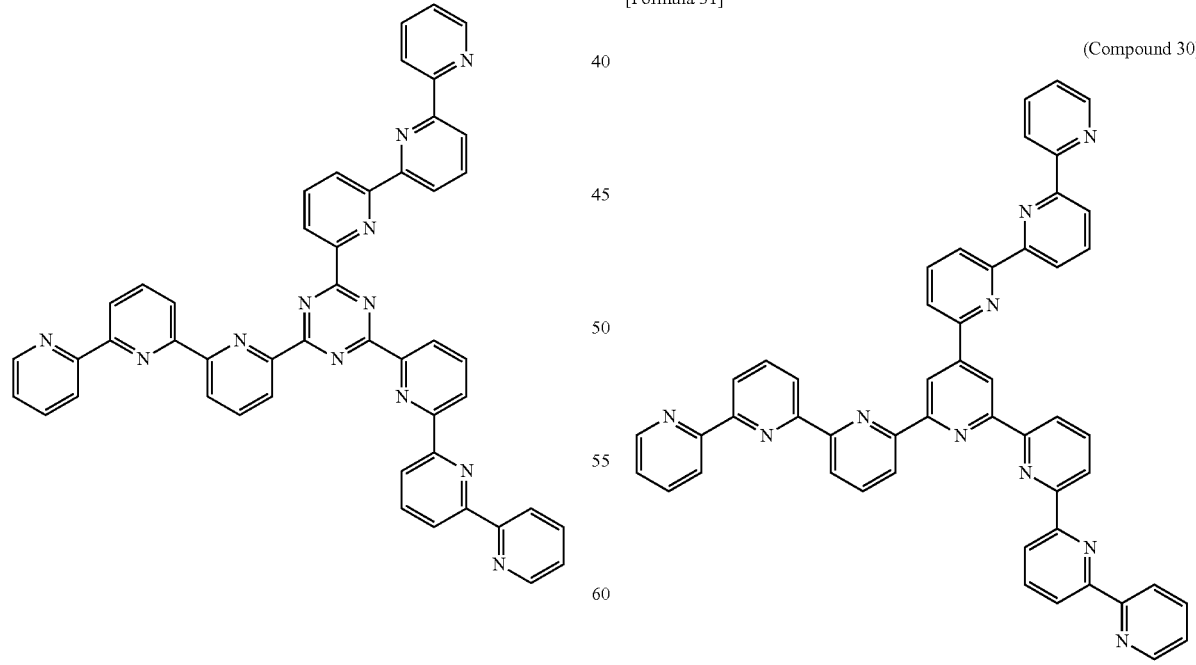
[Formula 31]
(Compound 30)

[Formula 32]
(Compound 31)
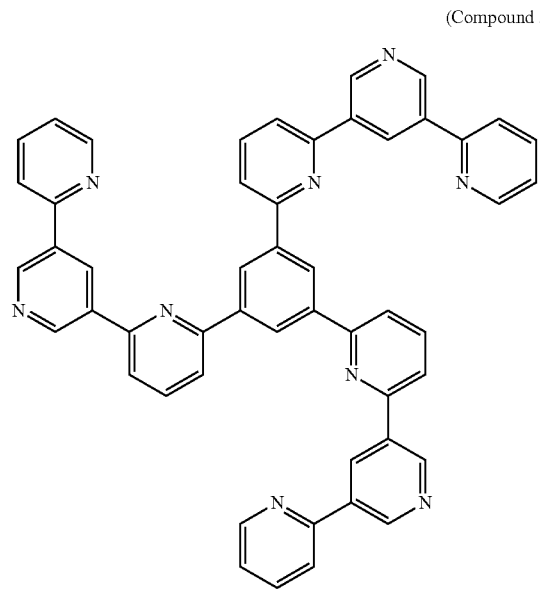
[Formula 33]
(Compound 32)
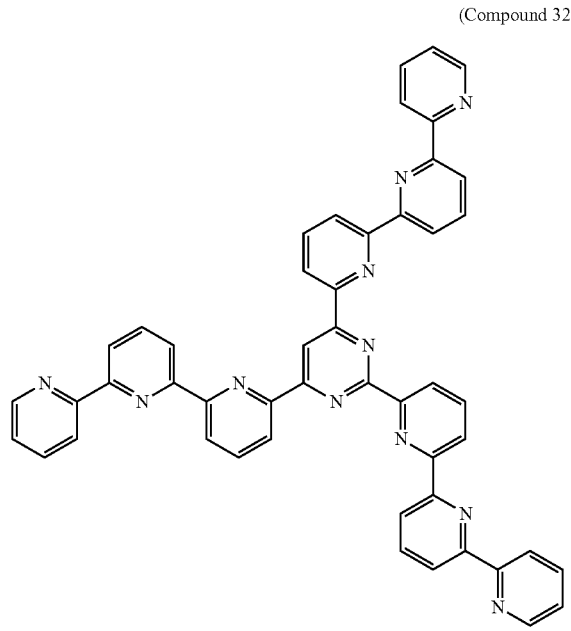
[Formula 34]
(Compound 33)
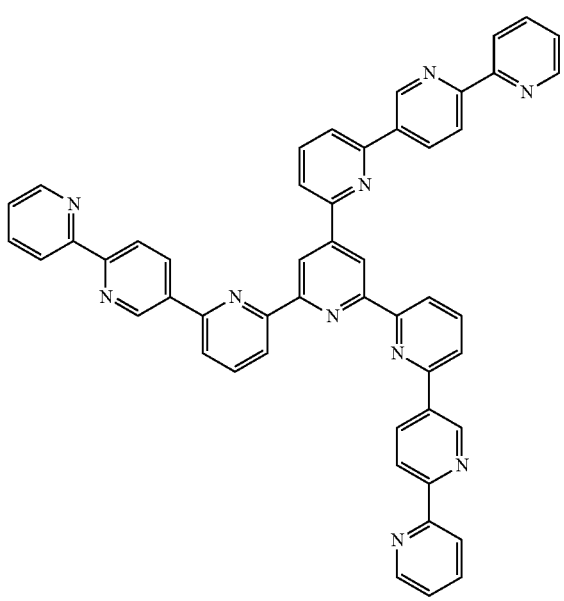
[Formula 35]
(Compound 34)

[Formula 36]
(Compound 35)
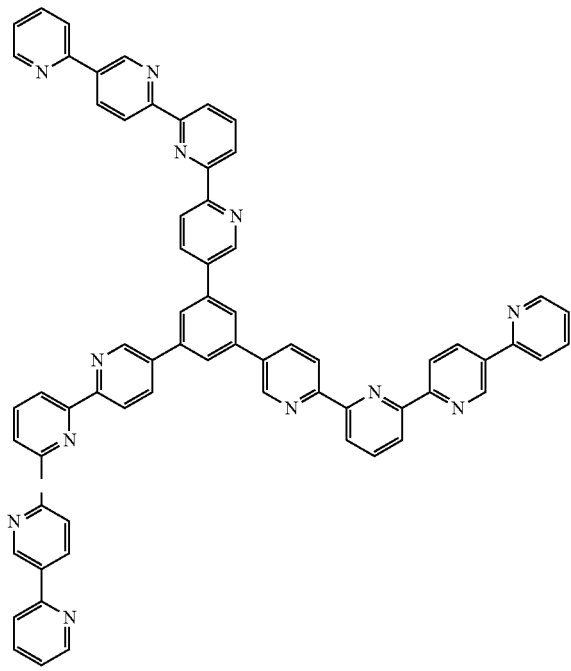
[Formula 37]
(Compound 36)
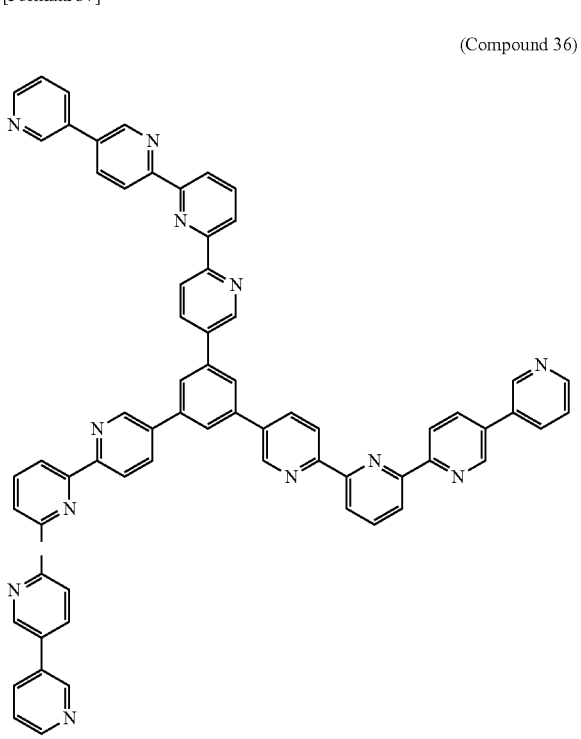
[Formula 38]
(Compound 37)
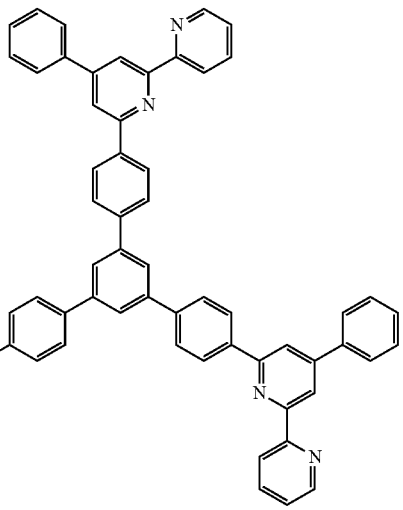
[Formula 39]
(Compound 38)
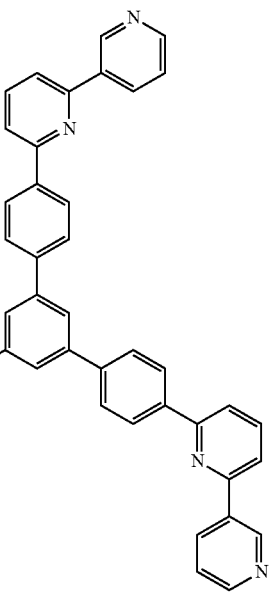

[Formula 40]
(Compound 39)
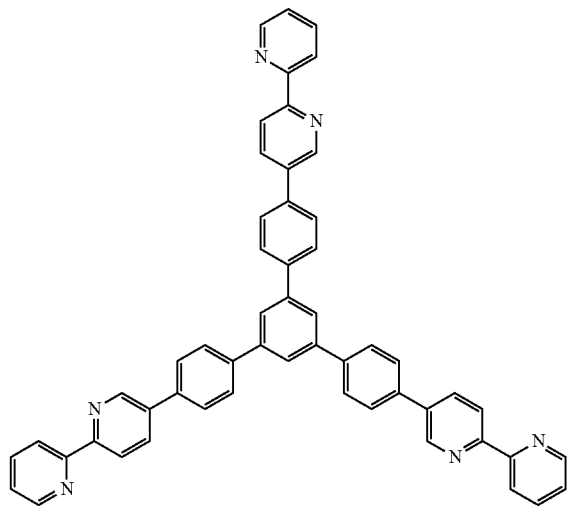
[Formula 41]
(Compound 40)
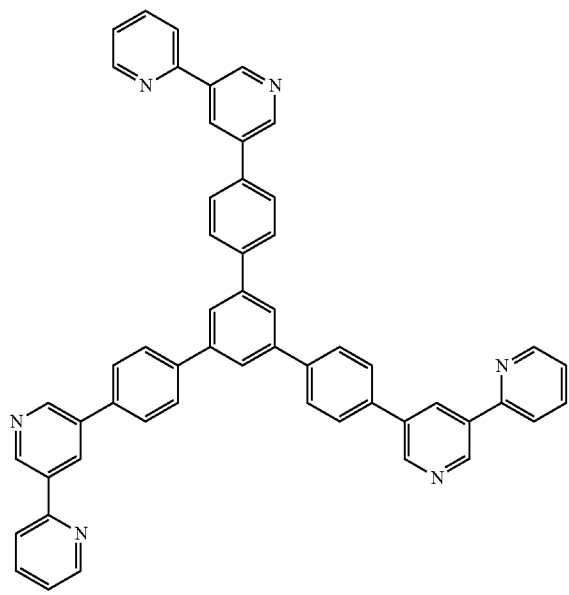
[Formula 42]
(Compound 41)
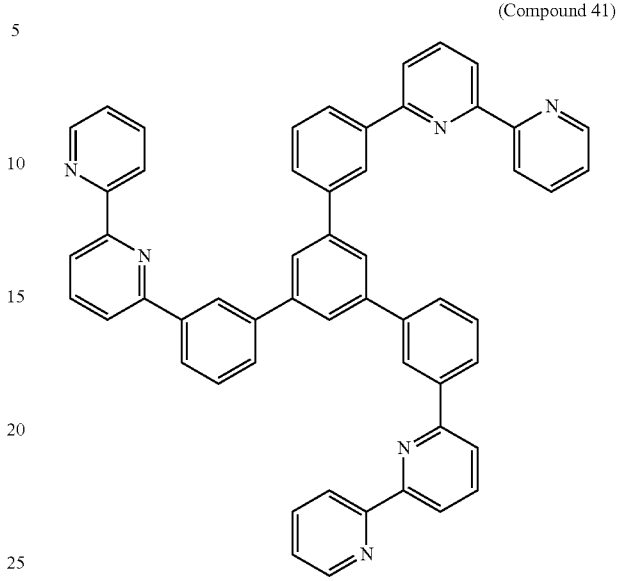
[Formula 43]
(Compound 42)
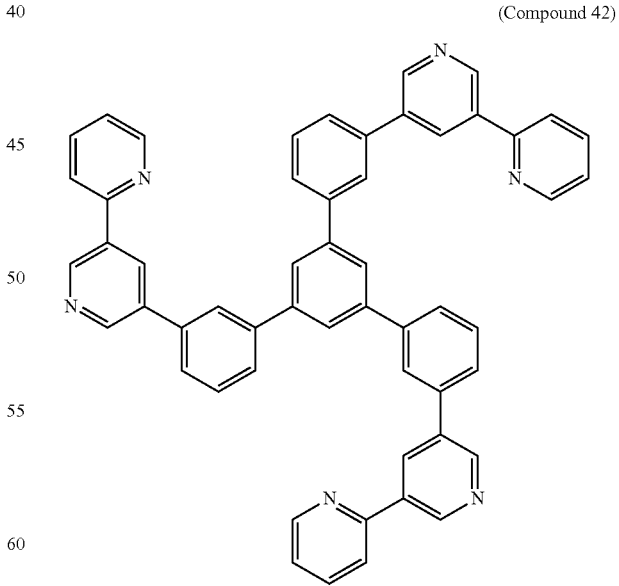

[Formula 44]

(Compound 43)

[Formula 45]

(Compound 44)

[Formula 46]

(Compound 45)

[Formula 47]

(Compound 46)

[Formula 48]

(Compound 47)

[Formula 49]
(Compound 48)
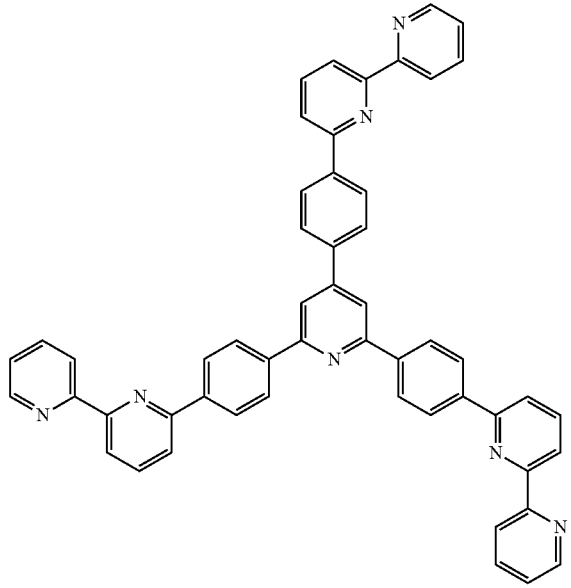
[Formula 50]
(Compound 49)
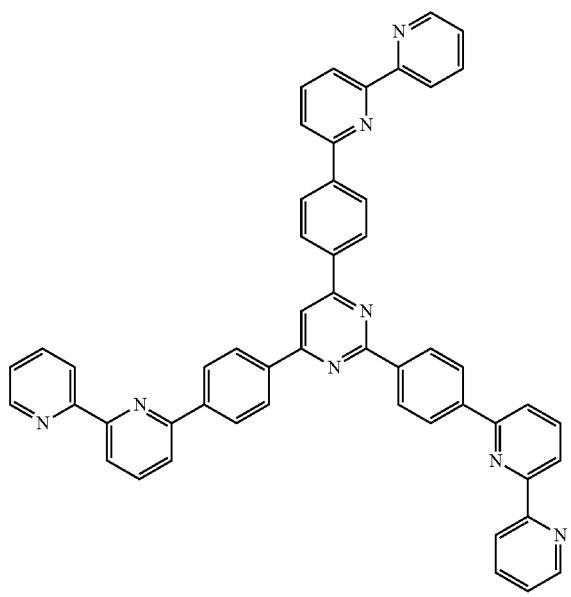
[Formula 51]
(Compound 50)
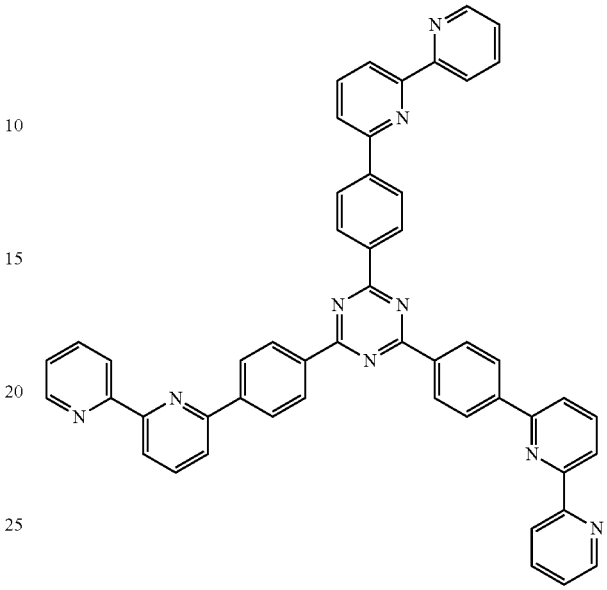
[Formula 52]
(Compound 51)
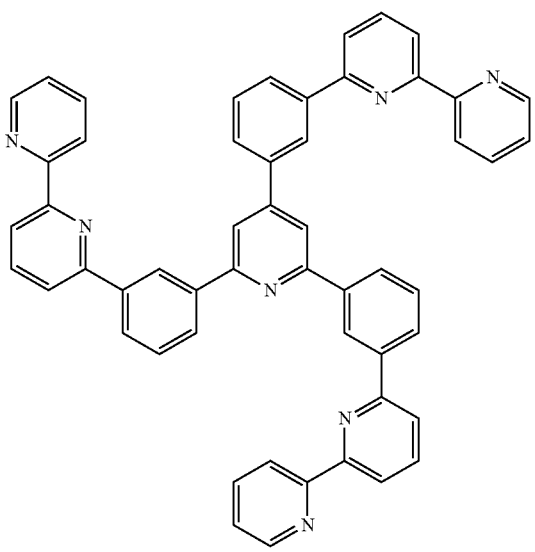

[Formula 53]
(Compound 52)
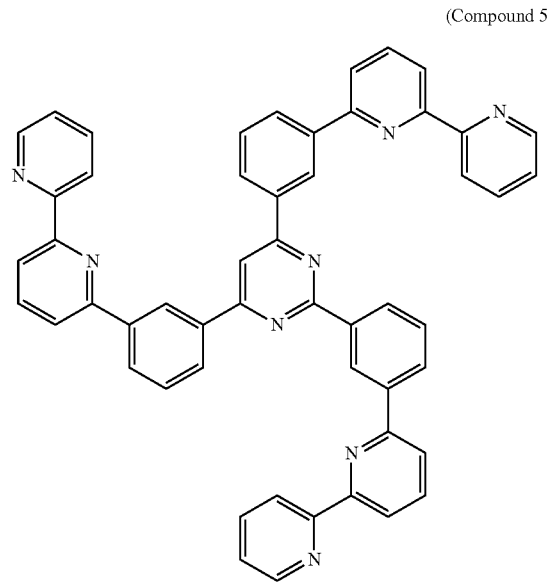
[Formula 54]
(Compound 53)
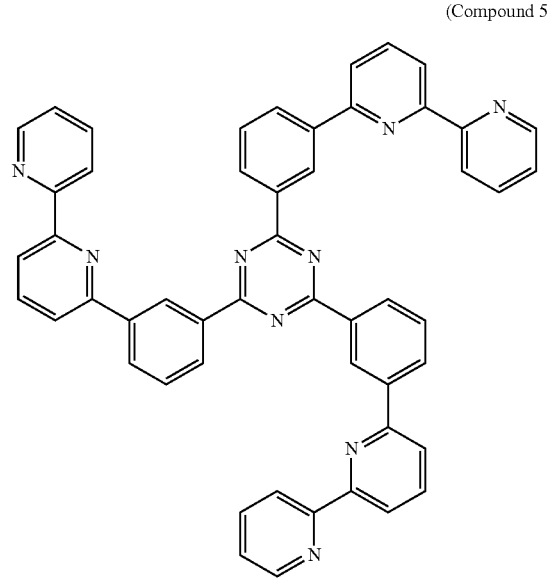
[Formula 55]
(Compound 54)
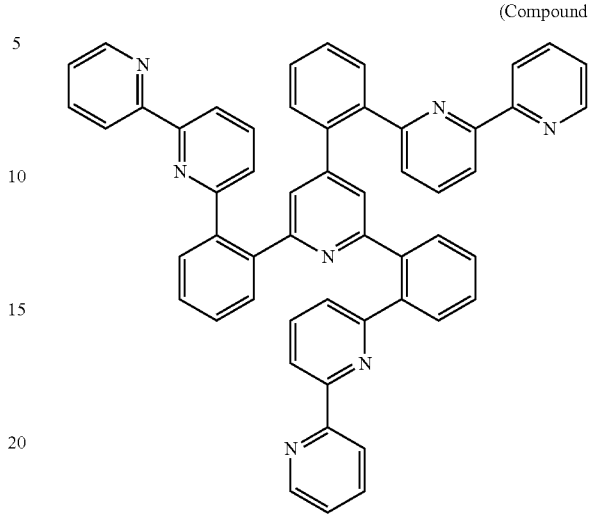
[Formula 56]
(Compound 55)
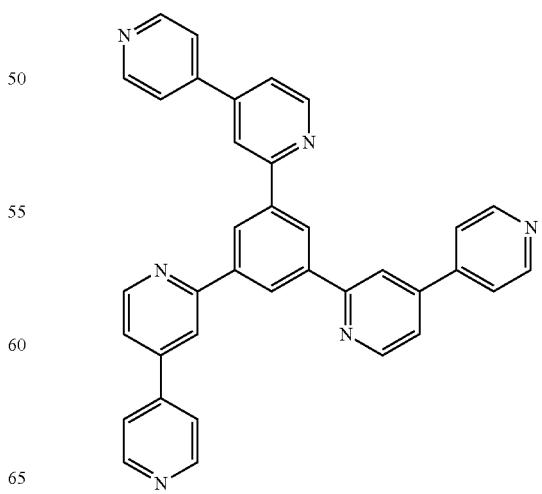
[Formula 57]
(Compound 56)

-continued

[Formula 58]

(Compound 57)

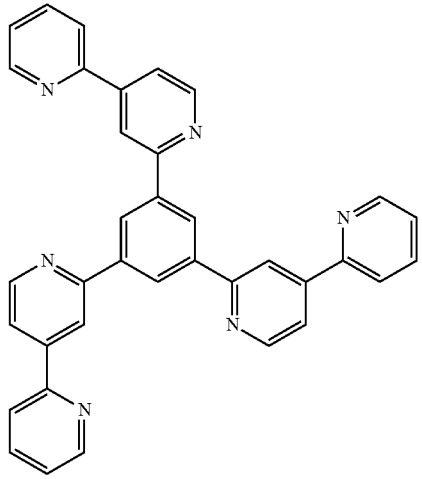

[Formula 59]

(Compound 58)

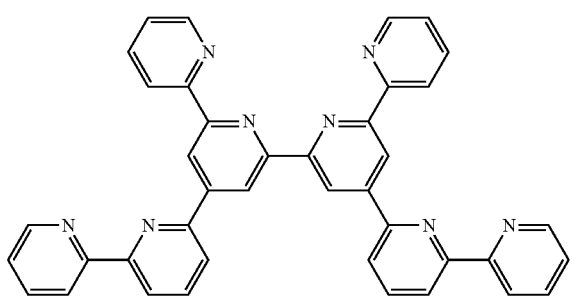

[Formula 60]

(Compound 59)

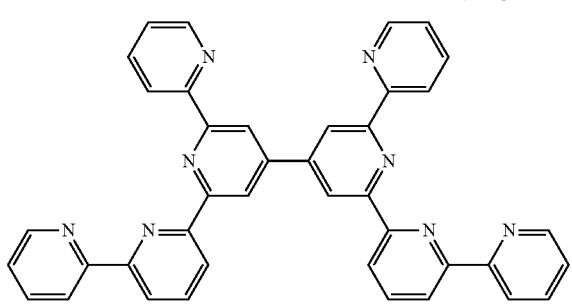

[Formula 61]

(Compound 60)

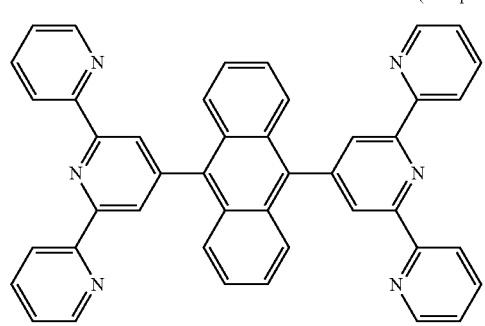

[Formula 62]

(Compound 61)

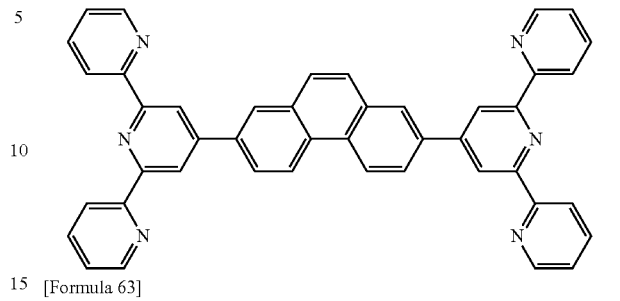

[Formula 63]

(Compound 62)

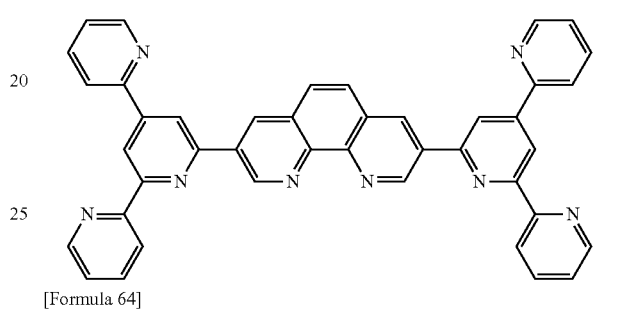

[Formula 64]

(Compound 63)

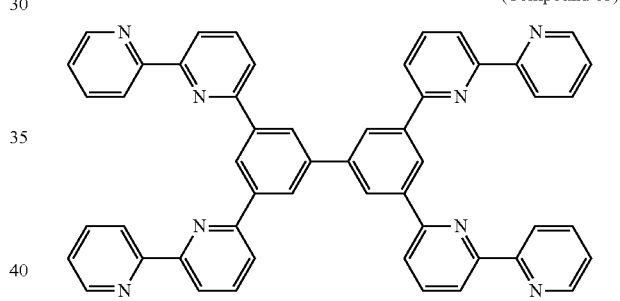

These compounds are purified through column chromatography purification, adsorption purification, or recrystallization or crystallization with solvent, etc. The compounds are identified through NMR analysis. DSC measurement (Tg) and melting point measurement are made for the physical data. The melting point can be an index of vapor deposition, and the glass transition point (Tg) can be an index of thin film stability.

For measurement of the melting point and the glass transition point thereof, the powder of the compound is analyzed with a high-sensitivity differential scanning calorimeter, Seiko Instruments' DSC6200.

The work function is measured as follows; A 100-nm thin film of the compound is formed on an ITO substrate, and analyzed with an atmospheric photoelectron spectrometer, Riken Keiki's AC3 Model. The work function can be an index of hole-blocking capability.

The structure of the organic EL device of the invention includes one comprising an anode, a hole transport layer, a light-emitting layer, a hole-blocking layer, an electron transport layer and a cathode in that order on a substrate, one having a hole injection layer between the anode and the hole transport layer, or one having an electron injection layer between the electron transport layer and the cathode. In the multilayer structure, some organic layers may be omitted; and for example, an anode, a hole transport layer, a light-emitting layer, an electron transport layer and a cathode may be formed in that order on a substrate.

As the anode of the organic EL device, used is an electrode material having a large work function, such as ITO or gold. For the hole injection layer, usable is copper phthalocyanine (hereinafter abbreviated as CuPc) as well as a material of a starburst-type triphenylamine derivative or the like, or a coating type material.

For the hole transport layer, usable are benzidine derivatives such as N,N'-diphenyl-N,N'-di(m-tolyl)-benzidine (hereinafter abbreviated as TPD) and N,N'-diphenyl-N,N'-di (α-naphthyl)-benzidine (hereinafter abbreviated as NPD), various triphenylamine tetramers, etc. As the hole injection/transport layer, usable is a coating type polymer material such as PEDOT/PSS.

For the light-emitting layer, the hole-blocking layer and the electron transport layer of the organic EL device of the invention, usable are compounds having a hole-blocking effect, for example, complexes with aluminium such as BAlq, thiazole derivatives, oxazole derivatives, carbazole derivatives, polydialkylfluorene derivatives, phenanthroline derivatives such as BCP, triazole derivatives such as TAZ and the like, in addition to the substituted bipyridyl compounds.

Using a conventional light-emitting material such as a complex with aluminum or a styryl derivative as the light-emitting layer and using the substituted bipyridyl compound as the hole-blocking layer and the electron transport layer provides high-efficiency organic EL devices. As the host material for the light-emitting layer, for example, usable is a fluorescent material such as quinacridone, coumarin or rubrene. As the phosphorescent material, usable are green phosphorescent materials such as iridium complex of phenylpyridine Ir(ppy)3; blue phosphorescent material such as FIrpic, FIr6; red phosphorescent material such as Btp2Ir (acac), etc. Regarding the host material for this, carbazole derivatives such as 4,4'-di(N-carbazolyl)biphenyl (hereinafter abbreviated as CBP), 4,4',4''-tri(N-carbazolyl)triphenylamine (hereinafter abbreviated as TCTA), 1,3-bis(carbazol-9-yl)benzene (hereinafter abbreviated as mCP) are usable as the hole-injecting/transporting host materials; and 2,2',2''-(1,3,5-phenylene)-tris(1-phenyl-1H-benzimidazole) (hereinafter abbreviated as TPBI) and the like are usable as the electron-transporting host material. With these, a high-efficiency organic EL device can be produced.

A conventional electron-transporting material may be superposed or co-deposited on the substituted bipyridyl compound to obtain an electron transport layer for use herein.

The organic EL device of the invention may have an electron injection layer. For the electron injection layer, usable is lithium fluoride or the like. As the cathode, usable is an electrode material having a low work function such as aluminum, or an alloy having a lower work function such as aluminum-magnesium is also usable as the electrode material for the cathode.

Embodiments of the invention will be described in detail with reference to the following Examples; however, not overstepping the scope and the sprit thereof, the invention should not be limited to the following Examples.

Example 1

Synthesis of 1,3,5-tris(2,2-'bipyridin-6-yl)benzene (compound 6)

8.6 g of 1,3,5-tribromobenzene, 25.0 g of bis(pinacolato) diboron, 24.1 g of potassium acetate, 250 ml of dimethyl sulfoxide previously dewatered with Molecular Sieves 4A, and 1.4 g of $PdCl_2$(dppf)-$CH_2Cl_2$ were put into a nitrogen-purged reactor, then heated, and stirred at 80° C. for 20 hours. After cooled to room temperature, the reaction liquid was put into 1000 ml of water, and stirred for 30 minutes. The precipitate was collected through filtration, and the precipitate was washed with methanol to obtain a crude product. The crude product was dissolved in 200 ml of ethyl acetate, the insoluble matter was removed through filtration, and the filtrated was concentrated to dryness to obtain 7.1 g (yield 57%) of a white powder, 1,3,5-tris(4,4,5,5-tetramethyl-[1,3,2]dioxaboroaran-2-yl)benzene.

2.5 g of the obtained 1,3,5-tris(4,4,5,5-tetramethyl-[1,3,2] dioxaboroaran-2-yl)benzene, 3.8 g of 6-bromo-[2,2']-bipyridine, 32.3 ml of aqueous 1 M potassium carbonate solution, 0.3 g of tetrakis(triphenylphosphine)palladium(0), 108 ml of toluene and 27 ml of ethanol were put into a nitrogen-purged reactor, and heated under reflux with stirring for hours. After cooled to room temperature, this was processed for liquid-liquid separation with 100 ml of water and 100 ml of toluene added thereto, and the organic layer was further washed with 100 ml of water. The organic layer was dewatered with anhydrous magnesium sulfate and then concentrated to obtain a crude product. The crude product was purified through column chromatography (carrier: NH silica gel, eluent: chloroform/n-hexane) to obtain 1.1 g (yield 38%) of a white powder, 1,3,5-tris(2,2'-bipyridin-6-yl)benzene (compound 6).

The structure of the obtained white powder was identified through NMR. The 1H-NMR data are shown in FIG. 1.

In the 1H-NMR (CDCl3), the following 24 hydrogen signals were detected: δ (ppm)=9.02 (3H), 8.76 (6H), 8.47 (3H), 7.99-8.04 (6H), 7.69 (3H), 7.37 (3H).

Example 2

Synthesis of 2,4,6-tris(2,2'-bipyridin-6-yl)-[1,3,5] triazine (compound 8)

5.0 g of [2,2']-bipyridine-6-carbonitrile, and 0.2 g of sodium hydride were put into a nitrogen-purged reactor, then heated and stirred at 150° C. for 7 hours. After cooled to room temperature, 15 ml of methanol was added to the reaction liquid, and further stirred for 1 hour. Subsequently, this was processed for liquid-liquid separation with 70 ml of water and 100 ml of chloroform added thereto, and the organic layer was further washed with 50 ml of water. The organic layer was dewatered with anhydrous sodium carbonate and concentrated to obtain a crude product. The crude product was purified through recrystallization with 70 ml of orthodichlorobenzene to obtain 2.3 g (yield 46%) of a pale yellow powder, 2,4,6-tris(2,2'-bipyridin-6-yl)-[1,3,5]triazine (compound 8).

Figure 2:
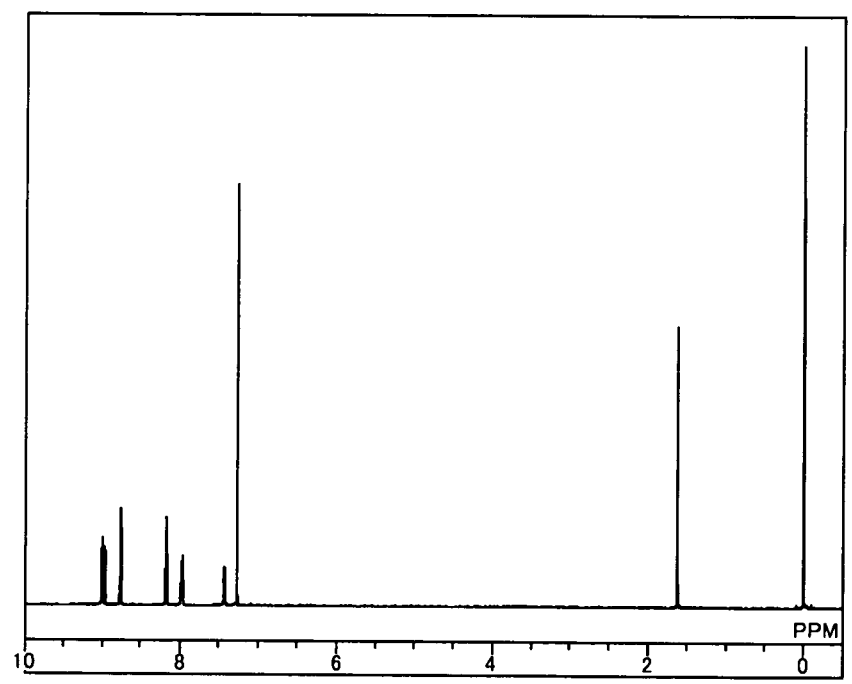
FIG. 2 This is a 1H-NMR chart of the compound (compound 8) of Example 2 of the invention.

The structure of the obtained pale yellow powder was identified through NMR. The 1H-NMR data are shown in FIG. 2.

In the 1H-NMR (CDCl3), the following 21 hydrogen signals were detected: δ (ppm)=8.99 (6H), 8.75 (6H), 8.17 (3H), 7.97 (3H), 7.42 (3H).

Example 3

Synthesis of 1,2,4,5-tetrakis(2,2'-bipyridin-6-yl)benzene (compound 15)

Like in the above-mentioned Example 1, 1,2,4,5-tetrakis (4,4,5,5-tetramethyl-[1,3,2]dioxaboroaran-2-yl)benzene was produced from 1,2,4,5-tetrabromobenzene and bis(pinacolato)diboron. 2.1 g of the obtained 1,2,4,5-tetrakis(4,4,5,5-tetramethyl-[1,3,2]dioxabororan-2-yl)benzene, 4.1 g of 6-bromo-2,2'-bipyridine, 21.8 ml of aqueous 2 M potassium carbonate solution, 0.2 g of tetrakis(triphenylphosphine)palladium(0), 120 ml of toluene and 30 ml of ethanol were put into a nitrogen-purged reactor, and heated under reflux with stirring for hours. After cooled to room temperature, this was processed for liquid-liquid separation with 100 ml of water and 300 ml of chloroform added thereto, and the organic layer was further washed with 100 ml of water. The organic layer was dewatered with anhydrous magnesium sulfate and then concentrated to obtain a crude product. The crude product was purified through column chromatography (carrier: NH silica gel, eluent: chloroform/n-hexane) to obtain 0.3 g (yield 12%) of a white powder, 1,2,4,5-tetrakis(2,2'-bipyridin-6-yl)benzene (compound 15).

Figure 3:
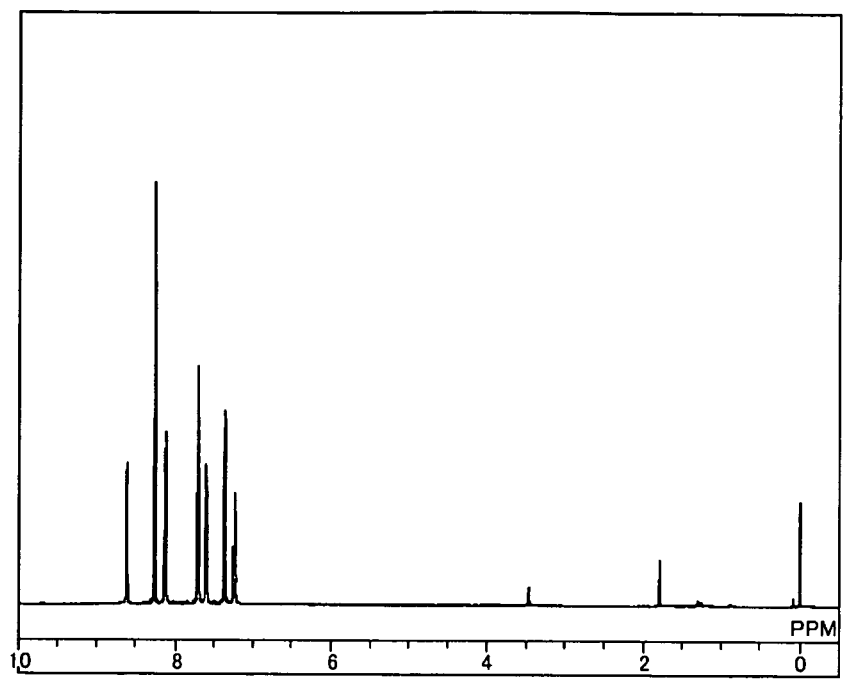
FIG. 3 This is a 1H-NMR chart of the compound (compound 15) of Example 3 of the invention.

The structure of the obtained white powder was identified through NMR. The 1H-NMR data are shown in FIG. 3.

In the 1H-NMR (CDCl3), the following 30 hydrogen signals were detected: δ (ppm)=8.62 (4H), 8.26 (6H), 8.12 (4H), 7.71 (4H), 7.60 (4H), 7.37 (4H), 7.23 (4H).

Example 4

Synthesis of 1,3,5-tris(2,2';6',2''-terpyridin-6-yl)benzene (compound 29)

3.0 g of 1,3,5-tris(4,4,5,5-tetramethyl-[1,3,2]dioxabororan-2-yl)benzene obtained in the above-mentioned Example 1, 6.2 g of 6-bromo-[2,2';6',2'']-terpyridine, 59.2 ml of aqueous 1 M potassium carbonate solution, 0.39 g of tetrakis(triphenylphosphine)palladium(0), 131 ml of toluene and 33 ml of ethanol were put into a nitrogen-purged reactor, and heated under reflux with stirring for hours. After cooled to room temperature, this was processed for liquid-liquid separation with 100 ml of water and 100 ml of toluene added thereto, and the organic layer was further washed with 100 ml of water. The organic layer was dewatered with anhydrous magnesium sulfate and then concentrated to obtain a crude product. The crude product was purified through column chromatography (carrier: NH silica gel, eluent: chloroform/n-hexane) to obtain 1.8 g (yield 35%) of a white powder, 1,3,5-tris(2,2';6',2''-terpyridin-6-yl)benzene (compound 29).

Figure 4:
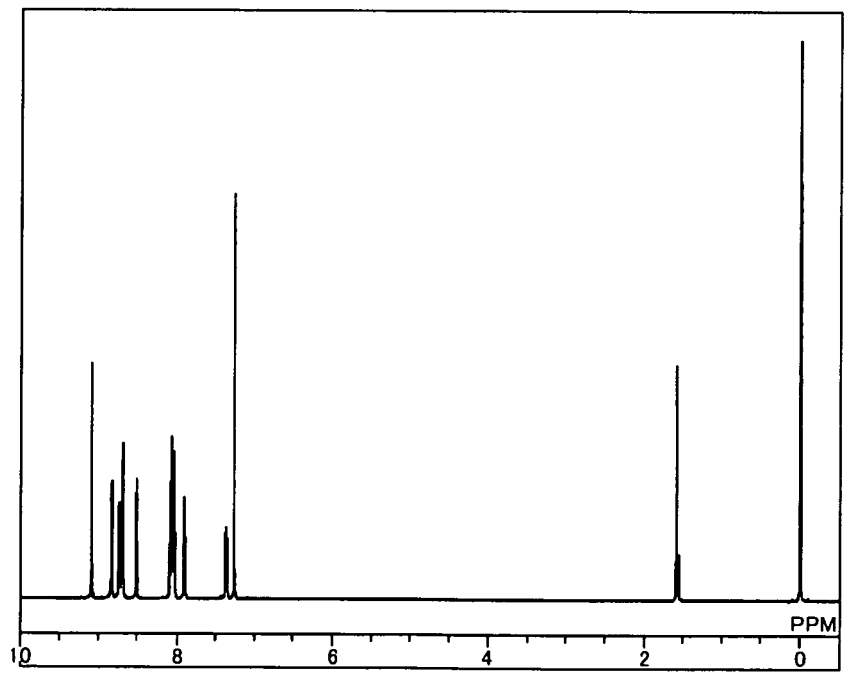
FIG. 4 This is a 1H-NMR chart of the compound (compound 29) of Example 4 of the invention.

The structure of the obtained white powder was identified through NMR. The 1H-NMR data are shown in FIG. 4.

In the 1H-NMR (CDCl3), the following 33 hydrogen signals were detected: δ (ppm)=9.09 (3H), 8.83 (3H), 8.74 (3H), 8.70 (6H), 8.51 (3H), 8.06 (9H), 7.90 (3H), 7.37 (3H).

Example 5

Synthesis of 3,5,3',5'-tetrakis(2,2'-bipyridin-6-yl)biphenyl (compound 63)

Like in the above-mentioned Example 1,3,5,3',5'-tetrakis(4,4,5,5-tetramethyl-[1,3,2]dioxabororan-2-yl)biphenyl was produced from 3,5,3',5'-tetrabromobiphenyl and bis(pinacolato)diboron. 3.2 g of the obtained 3,5,3',5'-tetrakis(4,4,5,5-tetramethyl-[1,3,2]dioxabororan-2-yl)biphenyl, 4.5 g of 6-bromo-2,2'-bipyridine, 28.7 ml of aqueous 2 M potassium carbonate solution, 0.3 g of tetrakis(triphenylphosphine)palladium(0), 110 ml of toluene and 25 ml of ethanol were put into a nitrogen-purged reactor, and heated under reflux with stirring for hours. After cooled to room temperature, this was processed for liquid-liquid separation with 100 ml of water and 300 ml of chloroform added thereto, and the organic layer was further washed with 100 ml of water. The organic layer was dewatered with anhydrous magnesium sulfate and then concentrated to obtain a crude product. The crude product was purified through column chromatography (carrier: NH silica gel, eluent: chloroform/n-hexane) to obtain 2.4 g (yield 64%) of a white powder, 3,5,3',5'-tetrakis(2,2'-bipyridin-6-yl)biphenyl (compound 63).

Figure 5:
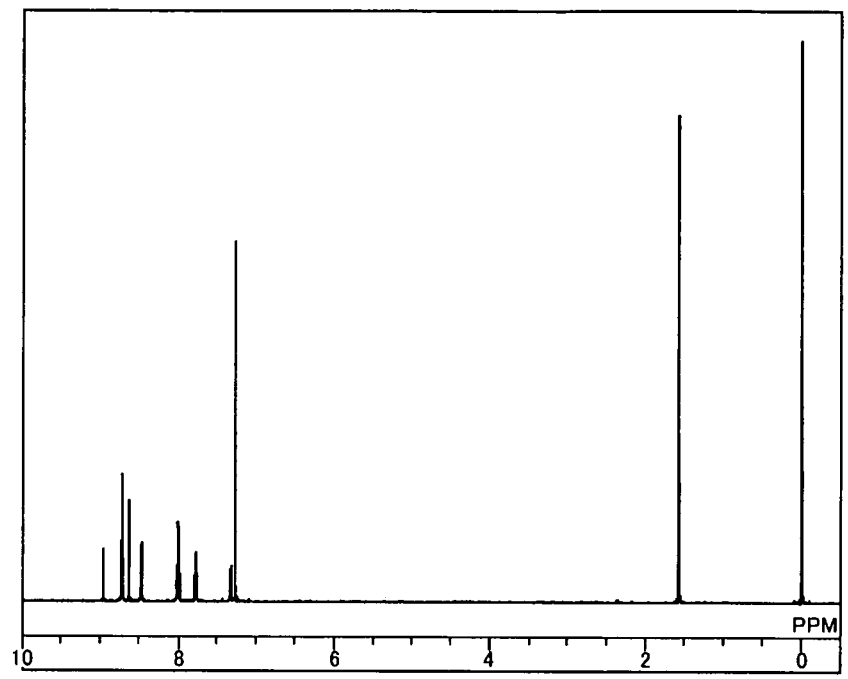
FIG. 5 This is a 1H-NMR chart of the compound (compound 63) of Example 5 of the invention.

The structure of the obtained white powder was identified through NMR. The 1H-NMR data are shown in FIG. 5.

In the 1H-NMR (CDCl3), the following 34 hydrogen signals were detected: δ (ppm)=8.96 (2H), 8.72 (8H), 8.63 (4H), 8.47 (4H), 8.00 (8H), 7.77 (4H), 7.32 (4H).

Example 6

The compounds of the invention were analyzed with a high-sensitivity differential scanning calorimeter, Seiko Instruments' DSC6200 to determine the melting point and the glass transition point thereof.

|  | Melting Point | Glass Transition Point |
| --- | --- | --- |
| Compound of Example 1 of the invention | 240° C. | 74° C. |
| Compound of Example 2 of the invention | 327° C. | 86° C. |
| Compound of Example 3 of the invention | 310° C. | 115° C. |
| Compound of Example 4 of the invention | 305° C. | 110° C. |
| Compound of Example 5 of the invention | 310° C. | none |

The compounds of the invention had a glass transition point of not lower than 70° C. or did not have a glass transition point. This indicates the stability of the compounds of the invention as thin films.

Example 7

Using the compound of the invention, a deposited film having a thickness of 100 nm was formed on an ITO substrate, and this was analyzed with an atmospheric photoelectron spectrometer (Riken Keiki's AC3 Model) to determine the work function thereof.

|  | Work Function |
| --- | --- |
| Compound of Example 1 of the invention | 6.45 eV |
| Compound of Example 2 of the invention | 6.70 eV |
| Compound of Example 3 of the invention | 6.58 eV |
| Compound of Example 4 of the invention | 6.60 eV |
| Compound of Example 5 of the invention | 6.38 eV |

As in the above, the compounds of the invention have a larger work function than that, 5.4 eV of ordinary hole-transporting materials such as NPD and TPD, and therefore have a larger hole-blocking ability.

Example 8

Figure 6:
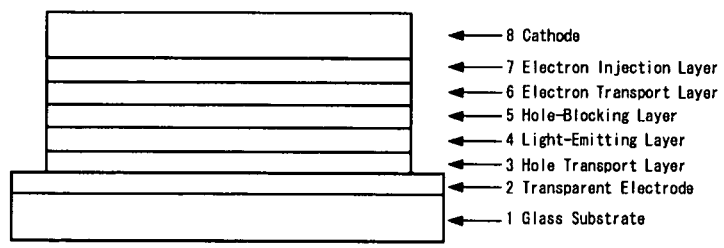
FIG. 6 This is a view showing the EL device constitution of Examples 8 to 11 and Comparative Example 1 to 2.

An organic EL device was produced by forming a hole transport layer 3, a light-emitting layer 4, a hole-blocking layer 5, an electron transport layer 6, an electron injection layer 7 and a cathode (aluminum electrode) 8 through vapor deposition in that order on a glass substrate 1 on which an ITO transparent electrode had been previously formed as an anode 2, as in FIG. 6. A glass substrate 1 with, as formed thereon, an ITO film having a thickness of 150 nm was washed with an organic solvent, and then its surface was washed through UV ozone treatment. This was set in a vacuum evaporation chamber, in which the pressure was reduced to 0.001 Pa or less.

Subsequently, NPD was deposited thereon as a hole transport layer 3 to have a thickness of about 30 nm at a vapor deposition rate of 6 nm/min. Further on it, CBP with $Ir(ppy)_3$, as controlled to have a composition ratio of 7% by weight, was deposited as a light-emitting layer 4 to have a thickness of about 40 nm at a vapor deposition rate of 6 nm/min. On the light-emitting layer 4, the compound of Example 1 of the invention (compound 6) was deposited as a hole-blocking layer also serving as an electron transport layer 5 and 6 to have a thickness of about 45 nm at a vapor deposition rate of 6 nm/min. On the hole-blocking layer/electron transport layer 5 and 6, lithium fluoride was deposited as an electron injection layer 7 to have a thickness of about 0.5 nm at a vapor deposition rate of 0.6 nm/min. Finally, aluminum was deposited to have a thickness of about 200 nm, thereby forming a cathode 8. The produced device was stored in a vacuum desiccator, and its characteristics were measured at room temperature in air.

Figure 7:
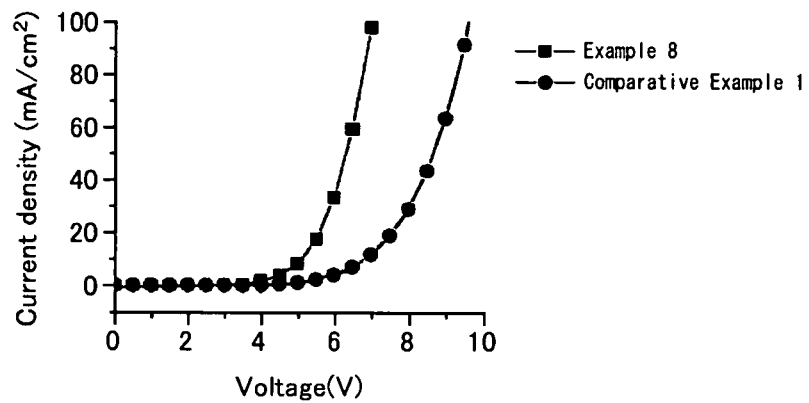
FIG. 7 This is a graph for comparing the voltage/current density characteristic between Example 8 and Comparative Example 1.
Figure 8:
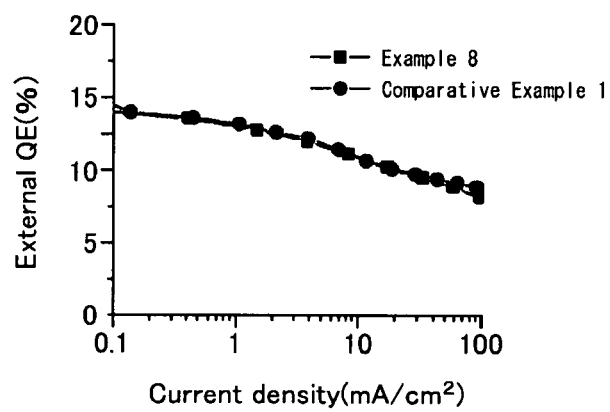
FIG. 8 This is a graph for comparing the current density/ external quantum efficiency between Example 8 and Comparative Example 1.

A direct voltage was applied to the organic EL device thus produced with the compound of Example 1 of the invention (compound 6), and the data of the light-emitting characteristics of the device are shown in FIG. 7 and FIG. 8. Specifically, the device gave light emission of 100 cd/m$^2$ from 3.3 V; and at 5.1 V, a current of 10 mA/cm$^2$ run through the device, and the device gave green light emission of 3900 cd/m$^2$. At the luminance, the external quantum efficiency of the device was 12%.

Comparative Example 1

For comparison, an organic EL device was produced under the same condition as in Example 8, for which, however, the hole-blocking layer 5 in Example 8 was changed to BCP, and the electron transport layer 6 was changed to $Alq_3$. Concretely, BCP was deposited as the hole transport layer 5 to have a thickness of about 15 nm at a vapor deposition rate of 6 nm/min, and $Alq_3$ was deposited as the electron transport layer 6 to have a thickness of about 30 nm at a vapor deposition rate of 6 nm/min. A direct voltage was applied to the produced organic EL device, and the data of the light-emitting characteristics of the device are shown in FIG. 7 and FIG. 8. Specifically, the device gave light emission of 100 cd/m$^2$ from 4.2 V; and at 7.0 V, a current of 10 mA/cm$^2$ run through the device, and the device gave green light emission of 3800 cd/m$^2$. At the luminance, the external quantum efficiency of the device was 12%.

As in the above, it is known that the organic EL device of the invention attained noticeable reduction in the drive voltage not lowering the external quantum efficiency thereof, as compared with the device in which BCP was used as the hole-blocking layer and $Alq_3$ generally used as an ordinary electron-transporting material was used as the electron transport layer.

Example 9

Like in Example 8, a glass substrate 1 with, as formed thereon, an ITO film having a thickness of 150 nm was washed with an organic solvent, and then its surface was washed through UV ozone treatment. This was set in a vacuum evaporation chamber, in which the pressure was reduced to 0.001 Pa or less. Subsequently, NPD was deposited thereon as a hole transport layer 3 having a thickness of about 30 nm to cover the transparent anode 2, at a vapor deposition rate of 6 nm/min. Further on it, mCP with FIr6, as controlled to have a composition ratio of 6% by weight, was deposited as a light-emitting layer 4 to have a thickness of about 40 nm at a vapor deposition rate of 6 nm/min. On the light-emitting layer 4, the compound of Example 1 of the invention (compound 6) was deposited as a hole-blocking layer also serving as an electron transport layer 5 and 6 to have a thickness of about 45 nm at a vapor deposition rate of 6 nm/min. On the hole-blocking layer/electron transport layer 5 and 6, lithium fluoride was deposited as an electron injection layer 7 to have a thickness of about 0.5 nm at a vapor deposition rate of 0.6 nm/min. Finally, aluminum was deposited to have a thickness of about 200 nm, thereby forming a cathode 8. The produced device was stored in a vacuum desiccator, and its characteristics were measured at room temperature in air.

A current density of 10 mA/cm$^2$ was applied to the organic EL device thus produced with the compound of Example 1 of the invention (compound 6). The data of the light-emitting characteristics of the device are summarized in Table 1.

Example 10

An organic EL device was produced in the same manner as in Example 9, in which, however, the compound of Example 3 of the invention (compound 15) was used for the hole-blocking/electron transport layer 5 and 6. A current density of 10 mA/cm$^2$ was applied to the produced organic EL device. The data of the light-emitting characteristics of the device are summarized in Table 1.

Example 11

An organic EL device was produced in the same manner as in Example 9, in which, however, the compound of Example 4 of the invention (compound 29) was used for the hole-blocking/electron transport layer 5 and 6. A current density of 10 mA/cm$^2$ was applied to the produced organic EL device. The data of the light-emitting characteristics of the device are summarized in Table 1.

Comparative Example 2

For comparison, an organic EL device was produced in the same manner as in Example 9, in which, however, TPBI was used for the hole-blocking/electron transport layer 5 and 6. A current density of 10 mA/cm$^2$ was applied to the produced organic EL device. The data of the light-emitting characteristics of the device are summarized in Table 1.

TABLE 1

|  |  | Voltage [V] (@10 mA/cm$^2$) | Luminance [cd/m$^2$] (@10 mA/cm$^2$) | Current Efficiency [cd/A] (@10 mA/cm$^2$) | Power Efficiency [lm/W] (@10mA/cm$^2$) |
|---|---|---|---|---|---|
| Example 9 | Compound 6 | 7.36 | 1011 | 10.11 | 4.04 |
| Example 10 | Compound 15 | 7.41 | 1029 | 10.29 | 4.36 |
| Example 11 | Compound 29 | 7.38 | 986 | 9.86 | 4.20 |
| Comparative Example 2 | TPBI | 8.73 | 881 | 8.81 | 3.17 |

As shown in Table 1, when a current density of. 10 mA/cm$^2$ was applied to the devices, the drive voltage of the devices comprising the compound of the invention was lower than the drive voltage, 8.73 V of the device comprising TPBI. In addition, when a current density of mA/cm$^2$ was applied thereto, the devices of the invention all had significantly higher data of luminance, current efficiency and power efficiency than that those of the device comprising TPBI.

As in the above, it is known that the blue phosphorescent organic EL devices of the invention are excellent in the current efficiency and the power efficiency and can attain remarkable reduction in the practical drive voltage, as compared with the device using an ordinary electron-transporting material TPBI.

INDUSTRIAL APPLICABILITY

The substituted bipyridyl compound of the invention shows an excellent electron-injecting/transporting performance and has an excellent hole-blocking ability, and its film is stable, and therefore, it is excellent as a compound for organic EL devices. When an organic EL device is produced, using the compound, then the drive voltage of the device can be lowered and the durability thereof can be improved. For example, the invention has made it possible to develop the application of the compound to electric home appliances and lightings.

The invention claimed is:

1. A substituted bipyridyl compound represented by the following general formula (1):

[Formula 1]

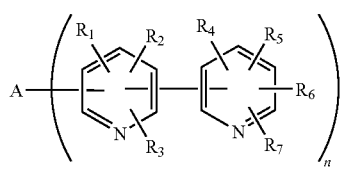

(1)

(wherein R~ to R7 may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a di- to tetravalent group of any of an acenaphthenyl group, or a trivalent group represented by the following general formula (2):

[Formula 2]

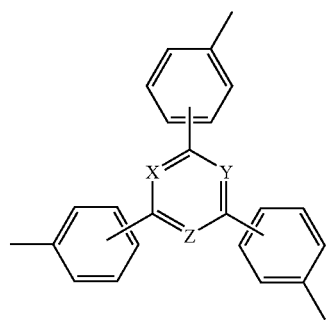

(2)

(wherein X, Y and Z each represents a carbon atom.

2. A substituted bipyridyl compound represented by the following general formula (3):

[Formula 3]

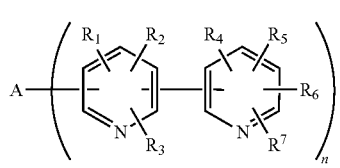

(wherein R$^1$ to R$^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a tri- or tetravalent group derived from biphenyl by removing 3 or 4 hydrogen atoms therefrom.

3. A substituted bipyridyl compound represented by the following general formula (4):

[Formula 4]

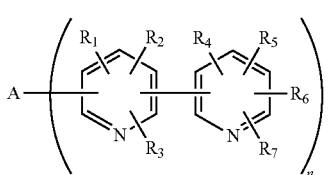

(wherein R$^1$ to R$^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A is a trivalent group represented by the following general formula (5):

[Formula 5]

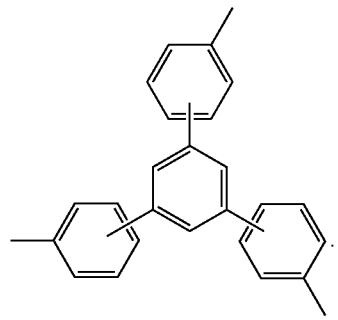

4. An organic electroluminescent device comprising a pair of electrodes and at least one organic layer sandwiched between them, wherein a substituted bipyridyl compound represented by the following general formula (8) is used as the constitutive material of at least one organic layer:

[Formula 8]

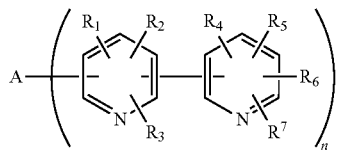

(wherein R1 to R7 may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a di- to tetravalent group of any of an acenaphthenyl group, or a trivalent group represented by the following general formula (9):

[Formula 9]

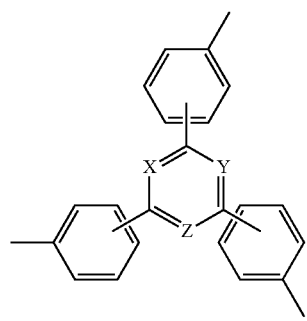

(wherein X, Y and Z each represents a carbon atom.

5. The organic electroluminescent device as claimed in claim 4, wherein the organic layer is an electron transport layer, and the compound of the general formula (1) is used as at least one constitutive material in the electron transport layer.

6. The organic electroluminescent device as claimed in claim 4, wherein the organic layer is a hole-blocking layer, and the compound of the general formula (1) is used as at least one constitutive material in the hole-blocking layer.

7. The organic electroluminescent device as claimed in claim 4, wherein the organic layer is a light-emitting layer, and the compound of the general formula (1) is used as at least one constitutive material in the light-emitting layer.

8. The organic electroluminescent device as claimed in claim 4, wherein the organic layer is an electron injection layer, and the compound of the general formula (1) is used as at least one constitutive material in the electron injection layer.

9. A substituted bipyridyl compound represented by the following general formula (10):

[Formula 10]

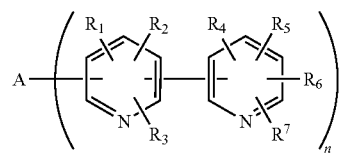

(wherein $R^1$ to $R^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a tri- or tetravalent, substituted or unsubstituted aromatic hydrocarbon group, and at least one of $R_1$ to $R_7$ is a substituted or unsubstituted aromatic heterocyclic group.

10. A substituted bipyridyl compound represented by the following general formula (11):

[Formula 11]

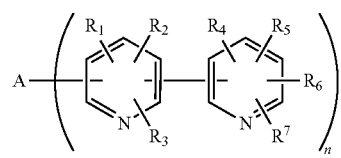

(wherein $R^1$ to $R^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a di- to tetravalent group of any of a pyridyl group, a furanyl group, a thienyl group, a quinolyl group, an indolyl group, group, a benzoxazolyl group, a benzothiazolyl group, a quinoxalyl group, a pyrazolyl group, a dibenzofuranyl group, a dibenzothienyl group, a naphthyridinyl group, and a phenanthrolyl group.

11. An organic electroluminescent device comprising a pair of electrodes and at least one organic layer sandwiched between them, wherein a substituted bipyridyl compound represented by the following general formula (13) is used as the constitutive material of at least one organic layer:

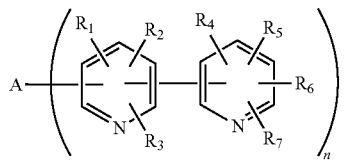

[Formula 13]

(wherein $R^1$ to $R^7$ may be the same or different, each representing a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n indicates an integer of from 2 to 4; A represents a di- to tetra-valent, substituted or unsubstituted aromatic hydrocarbon group, and at least one of $R^1$ to $R^7$ is a substituted or unsubstituted aromatic heterocyclic group.

* * * * *